(12) United States Patent
Tsuzukiyama et al.

(10) Patent No.: US 6,190,153 B1
(45) Date of Patent: Feb. 20, 2001

(54) ORIENTED FILM PRODUCING FACILITY WITH THICKNESS AND ORIENTATION CONTROL MEANS

(75) Inventors: Koji Tsuzukiyama, Sodegaura; Masanori Motooka, Ichihara; Toshiyuki Fujiwara, Ibaragi-ken; Michio Toriumi, Ichihara, all of (JP)

(73) Assignees: Mitsui Chemicals Inc.; Tohcello Co., Ltd.; Grand Polymer Co., Ltd., all of Tokyo (JP)

( * ) Notice: Under 35 U.S.C. 154(b), the term of this patent shall be extended for 0 days.

(21) Appl. No.: 09/069,732

(22) Filed: Apr. 30, 1998

(30) Foreign Application Priority Data

May 1, 1997 (JP) .................................... 9-113958
Nov. 26, 1997 (JP) .................................... 9-324742

(51) Int. Cl.[7] ........................... B29C 43/58; B29C 47/92; G01J 4/00; G01J 4/02; G01J 4/04
(52) U.S. Cl. ......................... 425/135; 425/141; 425/143; 425/145; 425/169; 425/325; 425/335; 264/40.1; 264/40.7; 264/410; 264/412; 356/364
(58) Field of Search ..................... 425/135, 141, 425/143, 145, 169, 325, 335; 264/40.1, 40.7, 410, 412; 356/364

(56) References Cited

U.S. PATENT DOCUMENTS

| | | | |
|---|---|---|---|
| 3,974,248 | * 8/1976 | Atkinson | 264/40.2 |
| 4,432,917 | * 2/1984 | Hungerford | 264/40.1 |
| 4,581,575 | * 4/1986 | Osaki et al. | 324/58.5 A |
| 4,909,630 | * 3/1990 | Gawrisch et al. | 356/364 |
| 4,931,982 | * 6/1990 | Hayashida et al. | 364/473 |
| 5,059,265 | * 10/1991 | Asakura | 156/64 |
| 5,529,730 | 6/1996 | Gross | 264/40.1 |
| 5,532,488 | * 7/1996 | Ishibashi et al. | 250/341.3 |
| 5,734,472 | * 3/1998 | Ito et al. | 356/364 |
| 5,779,962 | * 7/1998 | Andraschko et al. | 264/210.1 |

FOREIGN PATENT DOCUMENTS 1594710    8/1981   (GB) .

OTHER PUBLICATIONS

Patent Abstracts of Japan, vol. 16, No. 270, Jun. 17, 1992 and JP 04 065222A, Mar. 2, 1992, and Database WPI Derwent Publications Ltd., AN 92–120396.

* cited by examiner

Primary Examiner—Jan H. Silbaugh
Assistant Examiner—Michael I. Poe
(74) Attorney, Agent, or Firm—Birch, Stewart, Kolasch & Birch, LLP

(57) ABSTRACT

A drawing system in which a thickness and degree of orientation of an oriented film or the like is maintained in a uniform manner under a condition of a high speed, shortened is a time required from a time when a molding material is charged in an extruder and drawing started until a time when a film is taken up on a take-up apparatus, and a high quality film or the like is produced at a high speed and besides, a probability for a not-oriented or oriented film or the like to be broken down during drawing is reduced. A thickness and degree of orientation of a film are independently measured in thickness gauges and a film orientation measuring apparatus in a continuous manner after longitudinal drawing or lateral drawing and measured values are input to a computer. The computer input with the measured values respectively compares preset target values with the measured thickness and degree of orientation and a control operation to change a longitudinal draw ratio is conducted if the measured values are different from respective preset values based on results of comparison processing.

16 Claims, 9 Drawing Sheets

ORIENTED FILM PRODUCING FACILITY WITH THICKNESS AND ORIENTATION CONTROL MEANS

BACKGROUND OF THE INVENTION

1. Field of the Invention

The present invention relates to a drawing system in which a thermoplastic resin such as polypropylene, polyethylene or the like is molded into a shape of a film through a die by melt-extrusion with an extruder, a not-oriented film thus molded is drawn at a temperature equal to or lower than a melting point in longitudinal and lateral directions to orient molecules, and to an oriented film producing facility which comprises the drawing system, a measuring apparatus for measuring a thickness and an degree of orientation of a drawn film, and in which facility a predetermined control operation is performed on the drawing system based on measured values.

The present invention further relates to a high speed measuring method for measuring a birefringence, especially a birefringence, whose retardation which is larger than a measuring wavelength.

2. Description of the Background Art

A film used for packaging and the like has conventionally been produced in such a manner that a not-oriented film which is already molded into a shape of a thin film through die mounted on an extruder is subjected to drawing in longitudinal and lateral directions to orient molecules, whereby a bi-axially oriented film, whose mechanical characteristic, especially a strength is improved, made of polypropylene, vinylidene chloride resin, vinyl chloride resin, polystyrene, polyethylene terephthalate, polyethylene naphthalate, polyethylene, polyamide or the like is produced.

Here, the not-oriented film to be bi-axially oriented and the like are categorized in a crystalline resin and an amorphous resin and in the case of the crystalline resin a film is extruded at a temperature equal to or higher than a melting point and subjected to a rapid cooling while an amorphous condition is maintained in order to facilitate orientation. Then, the not-oriented film is drawn at a temperature equal to or lower than a melting point for orientation.

In the case of the amorphous resin, a film is extruded by an extruder at a temperature higher than a glass transition temperature so as to give the maximum degree of transparency. In order to orient the not-oriented film, the not-oriented film is cooled to a temperature in an elasticity range and drawn at the temperature for orientation.

A drawing machine which is used for orientation of a not-oriented film is, in a broad sense, categorized in a sequential bi-axial drawing type in which a longitudinal drawing is followed by a lateral drawing and a simultaneous bi-axial drawing type in which longitudinal and lateral drawings are simultaneously conducted. These two type machines are desired that a film which is oriented in a uniform manner in the two directions can be produced. In the case of the sequential drawing, while drawings are conducted in two stages, it is desirable that draw ratios of longitudinal and lateral directions and a temperature in respective stages can independently be changed in order to improve controllability on an degree of orientation and that the draw ratios can independently be changed in simultaneous drawing as well.

Recently, quality improvement on a film has increasingly been desired and it has furthermore been demanded that a film can be subjected to uniform drawing throughout the entire surface in both way, lengthwise and widthwise.

In order to cope with such desire and demand, there have been used a measuring apparatus for measuring a film thickness included in a drawing system and a film automatic control apparatus by which an extruder and a die are subjected to a predetermined control while a thickness is measured by the measuring apparatus.

The film automatic thickness control apparatus, as shown in FIG. 13, comprises: an extruder 50 which enables adjustment of a rotation number of a screw thereof, a die 51 mounted to the extruder, a die adjusting apparatus 52 for adjusting an opening degree of an extrusion mouth, a base film shaping apparatus 53 in which a not-oriented film is cooled to be hard, drawing machines 54, 55 which draws the not-oriented film which has been cooled to be hard is drawn in longitudinal and lateral directions, and a take-up apparatus 56 which takes up a drawn film, and β ray thickness gauges 57, 57 for measuring a thickness are respectively deployed at positions upstream of the longitudinal drawing machine 54 and downstream of a lateral drawing machine 55.

A thickness of a film is measured by these gauges 57, 57 and not only is a screw rotational number of the extruder 50 controlled based on a measuring data but an opening degree of the die 51 is controlled by an adjust bolt or the like.

There have been known measuring methods for birefringence as one of the means for evaluating a degree of orientation in an oriented high polymer film. Among such methods, if a retardation caused by a birefringence is larger than a measuring wavelength, a birefringence has to be computed from a spectrum of transmitted light when a high polymer film which is a specimen showing a birefringence is placed between a polarizing elements and therefore, as a high speed measuring method for measuring a birefringence, there has been known a method in which data of transmitted light spectrum measured by a multi-channel spectrometer are analyzed by use of a data processor such as a computer.

In a drawing machine equipped with the above mentioned film automatic thickness control apparatus, not only is a screw rotational speed of an extruder adjusted but an opening degree of a extrusion mouth of a die is adjusted based on measurement of a thickness only.

However, there is difficulty maintaining a thickness and an degree of orientation in a uniform manner along a direction perpendicular to a advancing direction of a base film, that is a width direction of the base film.

If a screw rotational speed is changed, a feed of molten resin is changed and thereby a global thickness of a base film can be controlled.

According to this method, while a thickness and a degree of orientation, as averages, of a drawn film can constantly be maintained, local fluctuations of thickness and degree of orientation cannot be prevented.

If an opening degree of the extrusion mouth of a die is narrowed by an adjust bolt such as a heat bolt, a thickness in a width direction can be controlled, but it entails reduction of a mass per a unit time of a not-oriented film during a time when the die extrusion mouth is narrowed, which is not to maintain a uniform degree of orientation over all the surface area.

In a drawing machine without the film automatic thickness control apparatus, fluctuations of thickness and degree of orientation along not only a width direction, but a longitudinal direction, of a film occurs. Therefore, there is a problem that the film during drawing has a high proportion of break-down by a drawing tension in longitudinal and lateral directions imposed on the film.

If a film is broken, an operation of a drawing system has to be stopped and, a broken film has to be removed, and not only is a time passed but labor is consumed before the system is restarted, which is a problem.

Especially, if a film is broken in a lateral drawing machine, necessary operations cannot be started since a temperature inside the machine is high and thereby there arises a problem that productivity is reduced.

There arises another problem that while a improvement toward a higher speed of drawing is desired for the purpose of cost down, unevenness in thickness and degree of orientation of a film is increased and a probability of film breakdown is increased if drawing is conducted at a high speed.

It has been desired to establish a production method for drawing an oriented film at a speed of 350 m/min or higher, or especially 500 m/min or higher.

SUMMARY OF THE INVENTION

The present invention has been made as improvement in light of the above mentioned problems.

That is, the present invention have objects to seek to achieve that a thickness and degree of orientation of a drawn film are maintained constant at a high speed, and that there is provided a drawing system, in which there is shortened a time elapsed from a time when a molding material is input to an extruder to a time when a film is drawn and taken-up in a take-up apparatus, and with which a high quality film or the like is produced at a high speed.

The present invention has an object to seek to achieve that there is provided a drawing system which has a reduced probability at which a film, whether drawn or not, or the like, is broken down in a drawing operation.

Besides, there has been desired a measuring method for measuring a birefringence in real time since a degree of orientation or a birefringence of a high polymer film is used in a production process each as a control item.

However, in a conventional measuring method for measuring a birefringence, it has been difficult measuring a birefringence in real time since much time is required for operations such as a transfer of transmitted light spectrum data to a computer and data processing in the computer.

It is an object of the present invention, to provide a measuring method for a birefringence capable of measuring a birefringence in real time.

The present invention has adopted the following means to achieve the objects:

An oriented film producing facility according to the present invention comprises: a facility for melting a molding material; an extruder having a die for shaping the molding material to a not-oriented film; a base film molding apparatus for producing a base film by cooling the not-oriented film shaped through the die; a longitudinal drawing machine for drawing the cooled base film in a longitudinal direction with a low speed roll and a high speed roll; and a lateral drawing machine for drawing the longitudinally drawn film in a lateral direction by holding both ends of the longitudinally drawn film.

The oriented film producing facility further comprises: a thickness gauge for measuring a thickness of the longitudinally drawn film in real time after the cooled base film is drawn in the longitudinal direction and an film orientation measuring apparatus for measuring an degree of orientation of the longitudinally drawn film in real time after the cooled base film is drawn in the longitudinal direction, wherein a signal corresponding to a thickness measured by the thickness gauge is output to a computer, a signal corresponding to an degree of orientation measured by a orientation measuring apparatus is output to the computer, the computer comprising a thickness comparison operation to compare a preset thickness with the measured thickness and an orientation comparison operation to compare a preset degree of orientation with the measured degree of orientation, and a control signal to change a longitudinal draw ratio in longitudinal drawing is output based on results of the respective comparison operations so as to coincide with a preset target value and a drawing condition is controlled in accordance with the control signal.

According to the oriented film producing facility, a thickness and degree of orientation of a film after a longitudinal drawing and a lateral drawing or independently measured in a continuous manner by a thickness gauge and an film orientation measuring apparatus, and measured values are input to a computer. The computer which has been input with the measured values compares preset values with the respective measured values of a thickness and a degree of orientation and performs a control operation to change a longitudinal draw ratio if the measured values are different from the respective preset values based on comparative results.

If a thickness of a film after longitudinal drawing can be controlled, a thickness and degree of orientation may be measured at any position on the film and can be measured during the longitudinal drawing.

Besides, a computer stores preset target values of a thickness as a profile in its memory, wherein the profile of thickness means a distribution of thickness in a width direction (lateral direction).

Next, a change in a longitudinal draw ratio is realized by a control operation of slowing or accelerating a rotational speed or speeds of a low speed roll or/and a high speed roll.

Control of a rotational speed can be attained by slowing a low speed roll singularly, accelerating a high speed roll singularly, slowing the low speed and accelerating the high speed roll, or slowing or accelerating both speeds in a proportional manner.

A rotational speed control of these rolls can be achieved by adjusting a rotational speed of a motor responsible for rotational drive of each roll.

As means for a change in a longitudinal draw ratio, a change is achieved by adjusting a draw gap between a low speed roll and a high speed roll or adjusting a draw angle of these rolls is available.

Here, the draw gap or draw angle is adjusted by displacing only a low speed roll in a direction, upward or downward, or leftward or rightward, or displacing only a high speed roll in a direction, upward or downward, or leftward or rightward.

In addition, both rolls may be displaced in a direction, upward or downward, and a direction, leftward or rightward. Movements of the rolls can be achieved such that a servo motor or the like is equipped to a roll displacement mechanism and the roll displacement mechanism is driven by rotation of the motor.

A longitudinal draw ratio can alternately be adjusted by adjusting pressing force of the cooled base film acting upon the high speed roll and the low speed roll.

In order to adjust a press-bonding strength, an air conditioner which sucks or jets air is provided in the vicinity of a contact position of the film to any or both of a high speed roll and low speed roll, and air is jet to reduce a press-bonding strength if the strength is large or air is sucked to increase a press-bonding strength if the strength is small.

In addition, a cold air is jet if a press-bonding strength is large, or hot air is jet or a flame is shot if a press-bonding strength is small. A plurality of nozzles are desirably provided to one roll.

In the oriented film producing facility, the thickness gauge for measuring a thickness of the longitudinally drawn film measures the thickness of the longitudinally drawn film on respective divided regions of the longitudinally drawn film along the lateral direction thereof after the longitudinal drawing and the orientation measuring apparatus measures the degree of orientation of the longitudinally drawn film on respective divided regions of the longitudinally drawn film along the lateral direction thereof after the longitudinal drawing.

Therefore, if measured thicknesses and degree of orientations thus obtained at positions in respective divided blocks in a lateral direction are different from respective target values, a control operation to change a longitudinal draw ratio is conducted so that thicknesses and degree of orientations in the respective blocks coincide with the respective target values. While a thickness and degree of orientation are measured by dividing a width of the film in a lateral direction into some regions, it is also possible that a film is divided into squares like those on a checkerboard by setting constant distances between adjacent boundaries in longitudinal and lateral directions on the film or regions at a constant distance between boundaries in a longitudinal direction only.

An oriented film producing facility according to the present invention comprises: a facility for melting a molding material; an extruder having a die for shaping the molding material to a not-oriented film; a base film molding apparatus for producing a base film by cooling a not-oriented film shaped through the die; a longitudinal drawing machine for drawing the cooled base film in a longitudinal direction with a low speed roll and a high speed roll; and a lateral drawing machine for drawing the longitudinally drawn film in a lateral direction by holding both ends of the longitudinally drawn film. The oriented film producing facility further comprises: a thickness gauge for measuring a thickness of the laterally drawn film in real time after the longitudinally drawn film is drawn in a lateral direction and an film orientation measuring apparatus for measuring an degree of orientation of the laterally drawn film in real time after the longitudinally drawn film is drawn in the lateral direction, wherein a signal corresponding to a thickness measured by the thickness gauge is output to a computer, a signal corresponding to an degree of orientation measured by the orientation measuring apparatus is output to the computer, the computer comprising a thickness comparison operation to compare a preset thickness with the measured thickness and an orientation comparison operation to compare a preset degree of orientation and the measured degree of orientation, and a control signal to change a lateral draw ratio in lateral drawing is output based on results of the respective comparison operations so as to coincide with a preset target value and a drawing condition is controlled in accordance with the control signal.

According to the oriented film producing facility, a thickness and degree of orientation of a film after each of a longitudinal drawing and a lateral drawing are independently measured in a continuous manner by a thickness gauge and an film orientation measuring apparatus and measured values are input to a computer. The computer which has been input with the measured values compares preset values with the respective values of a thickness and a degree of orientation and performs a control operation to change a longitudinal draw ratio if the measured values are different from the respective preset values based on comparative results.

The change in lateral draw ratio is achieved by adjusting a lateral draw angle in the lateral drawing.

Here, adjustment in a lateral draw angle is performed by adjusting only a leftward lateral draw angle if only a value of the leftward angle is different from a target value, or by adjusting only a rightward lateral draw angle if only a rightward value of the angle is different from a target value. Both draw angles, leftward and rightward, are simultaneously adjusted if both draw angles are respectively different from targets values.

Adjustment in draw angle can be achieved such that a servo motor or the like is equipped to an angle adjustment mechanism and the motor is rotated and the mechanism is driven by the rotation.

As another means for changing a lateral draw ratio, lateral draw ratios, left side and right side, are precisely adjusted. The adjustment in lateral draw speed is achieved by adjusting a rotational speed of a motor, which drives running rails to which a clip holding both ends of a film is fixedly mounted, for the purpose to adjust a magnitude of a moving speed of the clip.

In the oriented film producing facility, the thickness gauge for measuring a thickness of the laterally drawn film measures the thickness by dividing the laterally drawn film after the lateral drawing into regions along a lateral direction and the film orientation measuring apparatus measures the degree of orientation by dividing the laterally drawn film after the lateral drawing into regions along the lateral direction.

Therefore, if measured thicknesses and degree of orientations thus obtained at positions in respective divided blocks in a lateral direction are different from respective target values, a control operation to change a longitudinal draw ratio is conducted so that thicknesses and degree of orientations in the respective blocks coincide with the respective target values. While a thickness and degree of orientation are measured by dividing a width of the film in a lateral direction into regions, it is also possible that a film is divided into squares like those on a checkerboard by setting constant distances between adjacent boundaries in longitudinal and lateral directions on the film or regions at a constant distance between boundaries in a longitudinal direction only.

The oriented film producing facility has a function that, by the control signal, a heating temperature of the longitudinally drawn film is adjusted in correspondence to blocks of a heating apparatus for heating the longitudinally drawn film in the lateral drawing, the blocks being formed by dividing the heating apparatus in a predetermined manner.

An oriented film producing facility according to the present invention comprises: a facility for melting a molding material; an extruder having a die for shaping the molding material to a not-oriented film; a base film molding apparatus for producing a base film by cooling the not-oriented film shaped through the die; a longitudinal drawing machine for drawing the cooled base film in a longitudinal direction with a low speed roll and a high speed roll; and a lateral drawing machine for drawing the longitudinally drawn film in a lateral direction by holding both ends of the longitudinally drawn film.

A heating apparatus for the longitudinally drawn film in lateral drawing is divided into predetermined blocks, the thickness of the portion of the film corresponding to each of the blocks is measured by the thickness gauge in real time and the degree of orientation of the portion of the film corresponding to each of the blocks is measured in real time by the film orientation measuring apparatus, a signal corresponding to the thickness measured by the thickness gauge is output to the computer, a signal corresponding to an degree of orientation measured by the orientation measuring apparatus is output to the computer, the computer comprising a thickness comparison operation to compare a preset thickness of each block with the measured thickness of the block and an orientation comparison operation to compare a preset degree of orientation of each block and the measured degree of orientation of the block, and a control signal for each block is output based on respective results of the respective comparison operations so as to coincide with a preset target value and a drawing condition is controlled in accordance with the control signal.

The oriented film producing facility has a function to a heating temperature of each block is controlled in accordance with the control signal output for each block.

In an oriented film producing facility according the present invention, a heating area of a heating apparatus for heating a film in lateral drawing is divided at a predetermined distance between adjacent boundaries and a temperature is controlled in each heating region.

An oriented film producing facility according to the present invention has a function to adjust an opening degree of the die lips in accordance with the control signal.

In the oriented film producing facility according to the present invention, a magnitude of an opening degree is controlled in operation if a measured thickness and degree of orientation are different from respective preset values.

A magnitude of an opening degree of die lips are adjusted by an adjust bolt such as a heat bolt or the like and a local adjustment of the opening degree of a die lips is conducted by a plurality of heat bolts positioned along the directions, leftward and rightward, of the die lips.

An oriented film producing facility according to the present invention has a function to adjust a screw speed of the extruder in the case where a screw is equipped in the extruder in accordance with the control signal.

According to the oriented film producing facility of the present invention, a rotational speed of the screw inserted inside of the extruder is controlled in operation if a measured thickness and degree of orientation are different from respective preset values.

Here, a rotational speed of a screw is controlled by adjustment of a rotational speed of a motor responsible for rotational drive of the screw.

An oriented film producing facility according to the present invention is a facility in which the thickness gauge measures the thickness of a film by use of near-infrared absorption and a detective function of the thickness gauge outputs a signal corresponding to a thickness in 50 m sec, and the film orientation measuring apparatus measures a birefringence based on a principle for measuring a transmitted light spectrum of a film sandwiched by polarizing elements and measures data corresponding to the birefringence in 50 m sec to output a signal showing the data measured.

An oriented film producing facility uses the following the steps of: melting a molding material; extruding a not-oriented film by shaping the molding material with a die; molding a base film by cooling a not-oriented film shaped through the die; longitudinally drawing the cooled base film with a low speed roll and a high speed roll; laterally drawing the longitudinally drawn film by holding both ends; measuring a thickness of the longitudinally drawn film in real time after longitudinal drawing; measuring an degree of orientation of the longitudinally drawn film in real time after longitudinal drawing; outputting a signal corresponding to a thickness measured by the thickness measuring step to a computing step; outputting a signal corresponding to an degree of orientation measured by the degree of orientation measuring step to the computing step; comparing the preset thickness with the measured thickness, while comparing the preset degree of orientation with the measured degree of orientation in the computing step; outputting a control signal to change a longitudinal draw ratio in the longitudinal drawing based on results of the comparison operation so as to coincide with a preset target value; and controlling a drawing condition in accordance with the control signal.

An oriented film producing facility uses the following the steps of: melting a molding material; extruding a not-oriented film by shaping the molding material with a die; molding a base film by cooling a not-oriented film shaped through the die; longitudinally drawing the cooled base film with a low speed roll and a high speed roll; laterally drawing the longitudinally drawn film by holding both ends; measuring a thickness of the laterally drawn film in real time after lateral drawing; measuring an degree of orientation of the laterally drawn film in real time after lateral drawing; outputting a signal corresponding to a thickness measured by the thickness measuring step to a computing step; outputting a signal corresponding to a measured degree of orientation measured by the degree of orientation measuring step to the computing step; comparing the preset thickness with the measured thickness, while comparing the preset degree of orientation with the measured degree of orientation in the computing step; outputting a control signal to change a lateral draw ratio in the lateral drawing based on results of the comparison operation so as to coincide with a preset target value; and controlling a drawing condition in accordance with the control signal.

The oriented film producing facility further uses the following steps of: measuring the thickness of the film by use of near-infrared absorption; outputting a signal corresponding to the thickness measured in 50 m sec by its detective function; measuring a birefringence based on a principle for measuring a transmitted light spectrum of the film sandwiched by polarizing elements; measuring a data corresponding to the birefringence measured in 50 m sec to output a signal showing the data measured.

A birefringence measuring method is a method having a feature that a specimen having a birefringence is placed between a pair of polarizing elements, white light is projected from a side of one polarizing element of the polarizing elements contrary to the other side thereof opposed to the specimen and an interference spectrum of transmitted light emitted from a side of the other polarizing element contrary to the other side opposed to the specimen is analyzed to measure a birefringence and the method uses an apparatus comprising spectrum producing means for producing a spectrum from transmitted light; and a retardation computing circuit for outputting results of three parameters of a first extremum wavelength $\lambda 1$ and a second extremum wavelength $\lambda 2$ assuming extrema in the transmitted light spectrum, and the number M of extrema between the first and second extremum wavelengths, wherein a retardation R caused by the birefringence is computed from the three parameters, which are the outputs from the retardation computing circuit, according to the following equation and the birefringence of the specimen is further computed based on the retardation R.

$$R=(M-1)/2/(1/\lambda 1-1/\lambda 2)$$

wherein the number M of extrema includes extrema of the first extremum wavelength λ1 and the second extremum wavelength λ2 in number.

A birefringence measuring method is a method having a feature that a specimen having a birefringence is placed between a pair of polarizing elements, white light is projected from a side of one polarizing element contrary to the other side thereof opposed to the specimen and an interference spectrum of transmitted light emitted from a side of the other polarizing element contrary to the other side opposed to the specimen is analyzed to measure a birefringence and the method uses an apparatus comprising spectrum producing means for producing a spectrum from transmitted light; and a retardation computing circuit for outputting results of detection of three parameters of a first extremum wavelength λ1 and a second maximum wavelength λ2 assuming either maxima or minima in the transmitted light spectrum, and one number N of the numbers of maxima and minima between the first and second extremum wavelengths λ1, λ2, wherein a retardation R caused by the birefringence is computed from the three parameters, which are the outputs from the retardation computing circuit, according to the following equation and the birefringence of the specimen is further computed based on the retardation R.

$$R=(N-1)/(1/\lambda 1-1/\lambda 2)$$

wherein the number N of extrema includes extrema of the first extremum wavelength λ1 and the second extremum wavelength λ2 in number.

In a birefringence measuring method according to the present invention, the three parameters, that is a first extremum wavelength λ1 and a second maximum wavelength λ2, and the number M or N of extrema between the first and second extremum wavelengths, necessary for computation of a birefringence can be detected and output in real time, and besides the three parameters are detected by a exclusive-use retardation computing circuit and thereby a load imposed on a computer is reduced, so that a measurement of a birefringence can in real time be realized.

A birefringence measuring method according to the present invention is the spectrum producing means for producing a spectrum from transmitted light uses a multi-channel spectrometer as a spectroscopic method and an output signal from the multi-channel spectrometer can be output as an output of time-series in which an output time of the output signal corresponds to a wavelength and an output intensity of the output signal corresponds to an intensity of the transmitted light.

In a birefringence measuring method according to the present invention, the retardation computing circuit for outputting results of detection of three parameters of a first extremum wavelength λ1 and a second extremum wavelength λ2 assuming extrema in the transmitted light spectrum, and the number M or N of extrema between the first and second extremum wavelengths can comprise: a wavelength detecting section for computing a wavelength corresponding to an output time of a signal from the multi-channel spectrometer; a extremum detecting circuit for detecting a wavelength assuming an extremum in the transmitted light spectrum and outputting an extremum wavelength identification signal at a time corresponding to an extremum wavelength; a first extremum wavelength storage section for storing and outputting the first extremum wavelength λ1; a second extremum wavelength storage section for storing and outputting the second extremum wavelength λ2; and an extrema count section for counting and outputting the number M or N of extrema between the first extremum wavelength λ1 and the second extremum wavelength λ2.

In a birefringence measuring method according to the present invention, the extremum detecting circuit for detecting a wavelength assuming an extremum in a transmitted light spectrum can comprise: at least a differentiating circuit; a comparison operation circuit; and an extremum wavelength identification pulse generating section for generating a pulse at a time corresponding to an extremum wavelength according to a result of the comparison operation circuit, wherein the output of time-series output from the multi-channel spectrometer is differentiated in the differentiating circuit, a result of differentiation is compared with 0 V in the comparator; and an extremum wavelength identification pulse is generated in the extremum wavelength identification pulse generating section when the output of the comparator is changed.

In a birefringence measuring method according to the present invention, the first extremum wavelength storage section for storing and outputting the first extremum wavelength λ1 comprises: an input section for inputting two pieces of information of wavelength information from the wavelength detecting section and an extremum wavelength identification signal from the extremum detecting circuit; and an output section for outputting the first extremum wavelength λ1 stored, wherein the first extremum wavelength storage section is a circuit in which wavelength information is stored in synchronization with a first extremum wavelength identification signal in a range, in which detection of an extremum wavelength is conducted, among extremum wavelength identification signals output from the extremum detecting circuit at a time corresponding to an extremum wavelength according to a result in the extremum detecting circuit and there is updated an output value of an extremum wavelength information stored in synchronization with completion on the range in which detection of an extremum wavelength is conducted, the second extremum wavelength storage section for storing and outputting the second extremum wavelength λ2 comprises: an input section for inputting two pieces of information of wavelength information from the wavelength detecting section and an extremum wavelength identification signal from the extreme detecting circuit; and an output section for outputting a second extremum wavelength λ2 stored, wherein the second extremum wavelength storage section is a circuit in which extremum wavelength information is stored after sequentially updated in synchronization with an extremum wave identification signal in a range, in which detection of an extremum wavelength is conducted, among extremum wavelength identification signals output from the extremum detecting circuit at a time corresponding to an extremum wavelength according to a result in the extremum detecting circuit and there is updated an output value of an extremum wavelength information lastly stored in synchronization with completion on the range in which detection of an extremum wavelength is conducted, and the extreme count section for counting the number M or N of extrema between the first extremum wavelength λ1 and the second extremum wavelength λ2 comprises: an input section for inputting an extreme wavelength identification signal output from the extremum detecting circuit at a time corresponding to an extremum wavelength according to a result in the extremum detecting circuit; and an output section for outputting the number of extrema, wherein the extreme count section is a circuit in which there can be counted the number of extremum wavelength identification signals in a range, in which detection of an extremum wavelength is conducted, among extremum identification signals output from the extremum detecting circuit at a time corresponding to an extremum wavelength according to a result in the extremum detecting circuit and there can be updated an output value of the number of counts of an extreme wavelength identification signals output from the extremum detecting circuit at a time corresponding an extremum wavelength according to a result in the extremum detecting circuit in synchronization with completion on the range in which detection of an extremum wavelength is conducted.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE EMBODIMENT

First and second embodiments of an oriented film producing facility according to the present invention will be described in reference to FIGS. 1 to 12 below.

The First Embodiment (1) First of all, an outline of the oriented film producing facility of the first embodiment will be described.

Figure 1:
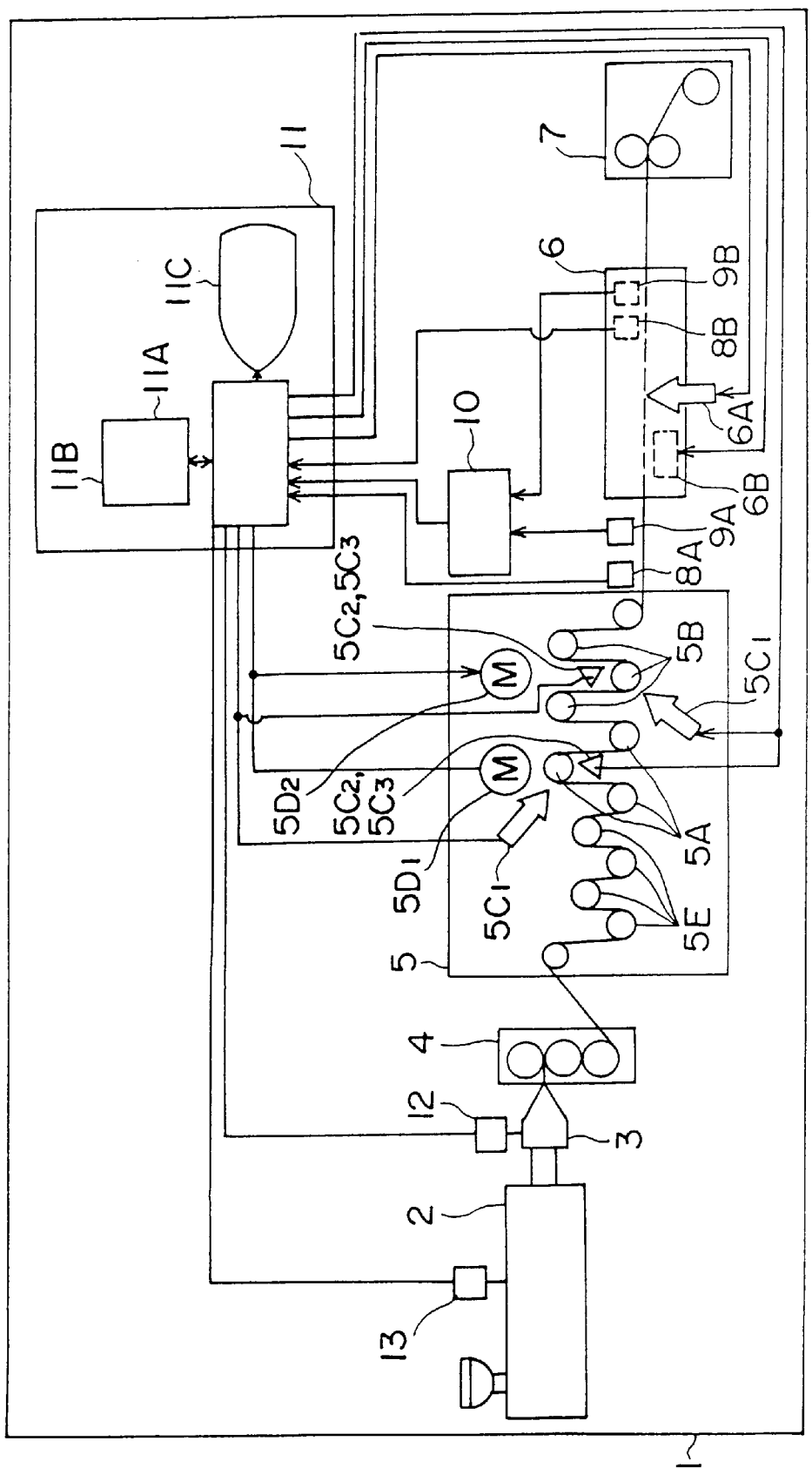
FIG. 1 is a view showing an oriented film drawing system according to the embodiment.

The oriented film producing facility, as shown in FIG. 1, comprises: an extruder 2, a die 3 mounted to an discharging end of the extruder 2; a base film shaping apparatus 4 which cools a not-oriented film discharged through the die 3; a sequential bi-axial drawing machine comprising a longitudinal drawing machine 5 which draws the base film in a longitudinal direction and a lateral drawing machine 6 which further draws a longitudinally drawn film in a lateral direction; and a take-up apparatus 7 which takes up a drawn film.

The oriented film producing facility 1 further comprises: thickness gauges 8A, 8B which measures a film already drawn, longitudinally or laterally; spectrometer 9A, 9B which obtains optical information from a film already drawn, longitudinally or laterally; a retardation processor 10 which computes a phase difference, and which is connected to the spectrometers 9A, 9B; a degree of orientation processing section, which connects to the thickness gauges 8A, 8B and the retardation processor 10 and which computes a degree of orientation from a thickness and a retardation both input; a computer 11 which outputs a predetermined control instruction; a screw rotational speed adjusting apparatus 13 in the extruder 2, a die adjusting apparatus 12, which adjusts an opening degree of the die; motors $5D_1$, $5D_2$ which rotate a roll of the longitudinal drawing machine 5; drivers $5C_1$, $5C_1$; which makes a drawing force for a film variable; air conditioners $5C_2$, $5C_2$, $5C_3$, $5C_3$, through which gas or the like is jet or sucked, a variable lateral draw mechanism 6A which makes a draw angle and draw speed in lateral drawing; and a lateral drawing machine 6, which is equipped with a temperature control mechanism 6 B for heating a film by dividing the film into blocks.

The computer 11 connects with the screw rotational speed adjusting apparatus 13, the die adjusting apparatus 12, the motors $5D_1$, $5D_2$, the drivers $5C_1$, $5C_1$, the air conditioners $5C_2$, $5C_2$, $5C_3$, $5C_3$, the lateral drawing apparatus 6 comprising the variable lateral draw mechanism 6A and the temperature control mechanism 6B.

A film orientation measuring apparatus is constituted of the thickness gauges 8A, 8B, the spectrometers 9A, 9B, the retardation computing circuit 10 and the computer 11 having an degree of orientation processing section.

(2) A constitution of the oriented film producing facility 1 according to the embodiment will be described in a concrete manner below.

i) The extruder 2 used in the oriented film producing facility 1 is equipped with: a hopper, though it is not shown, which is used for inserting a molding material in the form of powder or grains made of resin or the like; a heating cylinder for heating and melting the molding material; and a screw incorporated in the heating cylinder.

The screw is driven by the motor and the motor can be controlled so as to rotate at a desired rotational speed.

In the heating cylinder, for example an electrical heater is used for heating the interior of the cylinder. The total length of the heating cylinder is divided to several regions for independently heating each region in a controlled manner.

The extruder is classified into a single-spindle type and a multi-spindle type having the plural number of screws according to whether a single screw or a plurality of screws are used. As an extruder in the embodiment, any of a single-spindle type extruder, a double-spindle type extruder and a special type extruder can be used.

The die 3 which is mounted to the discharging end of the extruder 2 comprises: an flow inlet through which a molding material of, generally, a molten resin flows; a guiding route which guides the molding material to the die; an extruding mouth through which a film is extruded; and die lips which determines a shape of the extruding mouth.

A die 3 which is used for production of a film is a flat die or the like. An opening degree of the die can be adjusted by a heat bolt.

The base film shaping apparatus 4, which cools a shaped article, cools a molten resin as extruded through a slit of the die 3 in a uniform manner.

The sequential bi-axial drawing machine which draws a not-oriented film comprises a longitudinal drawing machine 5 and a lateral drawing machine 6 and the longitudinal drawing machine 5 comprises: heating rolls 5E, a low speed roll 5A disposed downstream of the heating rolls 5E, and high speed rolls 5B disposed downstream of the low speed rolls 5A.

The high speed rolls 5B rotate at a speed higher than the low speed rolls 5A so as to give a requested draw ratio and idle rolls are sometimes considered to be arranged in an associated manner with the low speed and high speed rolls so as to reduce neck-in due to drawing and prevent slippage of a film on a roll by making a draw distance short.

The heating rolls 5E are heated by electrical means or the like so that a base film is maintained at a predetermined temperature, which is required in drawing of the film. A draw speed, heating and drawing tension are adjustable in a proper manner for a film.

The motors drive rolls and the motors can be controlled so as to attain a desired rotational speed.

The drawing tension is adjusted with respect to its strength by respectively displacing rolls in directions, upward or downward and leftward or rightward.

The roll displacing mechanism is equipped with drivers $5C_1$, $5C_1$, such as servo motors or the like and the drivers $5C_1$, $5C_1$, are activated to drive the roll displacing mechanism in a controlled manner.

Gas such as air in the vicinity of a contact position between a film and a high speed roll and/or a low speed roll is sucked, or gas such as air is jet around the contact position to adjust a draw tension. A suction or jet port of the gas is connected to the air conditioner $5C_2$, $5C_2$, $5C_3$, $5C_3$ for sucking or jetting the gas. The air conditioner $5C_2$, $5C_2$, $5C_3$, $5C_3$ can jet hot air or cold air, or shoot a flame.

In the suction or jetting of gas, it is preferred that a plurality of jet or suction nozzles are respectively provided to areas of a film divided along a lateral direction.

Figure 10:
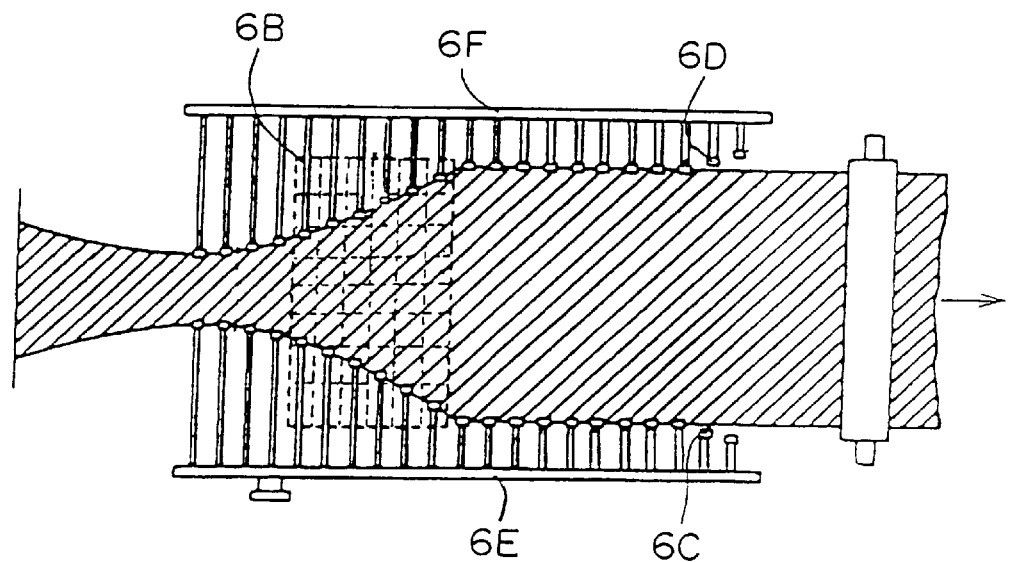
FIG. 10 is a plan view showing a lateral drawing machine.

The lateral drawing machine 6 is generally formed of 4 zones of heating, lateral drawing, heat treatment and cooling and, as shown in FIG. 10, in the first stage both ends of a longitudinally drawn film are held by clips 6C, 6D; the film enters the heating zone with a given width thereof and heated to a drawing temperature by a heater 6B; in the drawing zone the film is drawn in a lateral direction according to an opening angle of the clips 6C, 6D respectively on the left and right side of the film; the clips run through the heat treatment zone; and then run through the cooling zone.

The lateral drawing machine 6 is provided with a variable lateral draw mechanism 6A, which enables a change in draw angle or draw speed any time if necessary. The draw angle can be changed in such a manner that a servo motor or the like is equipped to the mechanism and the motor is activated to drive the mechanism.

The draw speed can be changed by adjusting a rotational speed of a motor which drives running rails 6E, 6F to which the clips are fixedly mounted, said clips holding both ends of a film.

Control of the rotational speed of the motors are performed by use of a rotational speed control method, such as bridge servo, proportional current control, DC tacho+voltage proportional control or frequency synchronization control, PLL control or the like; a power control method, such as PWM control, vector control, pulse control, bipolar drive or the like; or a combination thereof.

In addition, a control method, such as microstep drive, inverter drive, multi-phase drive or the like can also be used.

In the lateral drawing machine 6, the heater 6B mounted inside the machine is divided to blocks and there is provided a temperature control mechanism which enables a temperature in each block to be individually controlled.

The take-up apparatus 7, which takes up drawn film, may be of several different types are named: a nip-roll type take-up machine, a multi-stage nip-roll type take-up machine, a belt type take-up machine, multi-point drive roller type take-up machine, caterpillar type take-up machine and the like, depending upon the respective shapes and other conditions of the films used.

ii) The thickness gauges 8A, 8B which continuously measure a thickness of a film in real time comprise a light source, though it is not shown, emitting light of a wavelength used in measurement, a light detecting apparatus and a processor, and in addition a light guiding apparatus such as an optical fiber or the like is used in the system if necessary.

A film thickness is determined by measuring a transmittance ratio between a first wavelength of light in the near infrared region which is absorbed by a film and a second wavelength in the vicinity of the first wavelength which is not absorbed by the film.

A precise measurement of a film thickness can be achieved by a transmittance ratio between the two light beams of wavelengths even when a transmittance is changed due to light scattering caused by a surface profile including a concavity and a convexity.

The reason why it is considered that degrees of light scattering of two beams having different wavelengths close to each other are almost equal to each other and therefore a transmittance ratio is not changed even if each transmittance is changed by light scattering on such an irregular surface profile.

While two wavelengths, one to be absorbed by a film and the other not to be absorbed by the film, are selected at need, it is preferable to use a wavelength of 1.72 $\mu$m which is of a secondary mode of the C–H stretching vibration as a wavelength of light to be absorbed and a wavelength of 1.60 $\mu$m as a wavelength of light not to be absorbed.

All that is required for a light source used in a measuring apparatus is that the light source can emit light of these wavelengths and therefore, a halogen lamp, a xenon lamp or the like can be used.

A light detecting apparatus comprises a wavelength selecting element and a light detector. As the wavelength selecting element, a spectroscope, an interference filter or the like can be used, but among them an interference filter is preferred since it is small and easy to handle.

What is all required as a light detector is to enable detection of light of a wavelength in use and as a detecting element for the near infrared light, there are named: thermopile, a bolometer, pneumatic detecting element, pyroelectricity detecting element and the like and as a quantum type detecting element, there are named: detectors such as made of PbS, PbSe, Ge, InGaAs, InAs, InSb and the like.

In the processor, a signal from the light detector is received through an A/D (analogue/digital) converter or the like and the signal from the light detector is converted to a transmittance to compute a film thickness d according to the following equation:

$$d = C \cdot \ln(TA/TB)$$

wherein d is a film thickness, C is a constant, TA is a transmittance at a wavelength of light not to be absorbed and TB is a transmittance at a wavelength of light to be absorbed.

As the thickness measuring method, there can be used a β thickness gauge, a γ thickness gauge, an infrared thickness gauge, laser thickness gauge and the like.

An apparatus 9A, 9B for measuring an degree of orientation of a film in real time comprises: thickness gauges 8A, 8B, an apparatus for measuring a retardation caused by a birefringence, and a degree of orientation processing section provided in a control section 11, and as occasion demands, a light guiding apparatus such as an optical fiber is used.

Measurements 9A, 9B of an degree of orientation are carried out by computing a birefringence Δn of a film in the degree of orientation processing section based on a film thickness d measured by the thickness gauges 8A, 8B and a birefringence retardation R(=Δn·d) measured by the apparatus for measuring a birefringence retardation.

Since there is a correlation between a birefringence Δn of a film and a degree of orientation of the film, the degree of orientation can be obtained by converting the birefringence Δn to the degree of orientation in the degree of orientation processing section.

As for the thickness gauges 8A, 8B, the above mentioned thickness gauges can be used, but exclusive-use thickness gauges for degree of orientation measurement can be used in addition to the above mentioned thickness gauges.

An apparatus for measuring a retardation caused by a birefringence for realization of a birefringence measuring method according to the present invention comprises: a white light source; a polarizing element, a light detecting element, a spectroscope, a retardation computing circuit for outputting results of detection of three parameters of a first extremum wavelength λ1 and a second extremum wavelength λ2 assuming extrema in the transmitted light spectrum, and the number M (including extrema of the first and second extremum wavelengths λ1, λ2) of extrema between the first and second maximum wavelengths and a computer for computing a birefringence from three parameters which are outputs from the retardation computing circuit.

The polarizing element is used to transform light from the white light source to a linearly polarized light and the linearly polarized light is passed through a film having a birefringence placed between the polarizing element and the light detecting element to change transmitted light to elliptically polarized light by a birefringence of the film.

The elliptically polarized light is transmitted through the light detecting element and an intensity of the transmitted light is changed according to a degree of elliptical polarization. That is, a film showing a birefringence is inserted between a polarizing element disposed in a cross Nicols configuration and a light detecting element and when a light detecting element and light is projected on the polarizing element side, a light intensity spectrum of transmitted light on the light detecting element side is expressed by the following equation:

$$I = I_0 \cdot (\sin 2\theta)^2 \cdot \{\sin(\delta/2)\}^2 \tag{1}$$

wherein $I_0$ is a light intensity of transmitted light through the polarizer, θ is an optical axis angle of a film having a birefringence, δ is a phase difference by a birefringence (=2π·Δn·d/λ), Δn is a birefringence of the film, d is a film thickness and λ is a wavelength of light.

In the case where θ is not nπ/2 (where n is an integer), a spectrum of transmitted light show maxima and minima. The maxima and minima are when the retardationδ satisfies the following equation based on the equation (1).

$$\delta = 2\pi \cdot R/\lambda = m \cdot \pi \tag{2}$$

wherein R(=Δn·d) is a value of a retardation by a birefringence expressed in terms of a length and m is an integer, wherein when m is an even number, (1) assumes a minimum and when m is an odd number, (1) assumes a maximum.

If it is assumed that extrema are shown at two wavelengths, λ1, λ2 (λ2>λ1) and if wavelength dependence of a birefringence is neglected, the following equations are established:

$$\delta 1 = 2\pi \cdot R/\lambda 1 = m1 \cdot \pi$$

$$\delta 2 = 2\pi \cdot R/\lambda 2 = m2 \cdot \pi$$

If differences are respectively computed on both sides of the two equations, the following equation is further introduced:

$$2 \cdot R \cdot (1/\lambda 1 - 1/\lambda 2) = (m1 - m2) \tag{3}$$

In the equation (3), m2m1 is the number obtained after the number M of extrema present between λ1, λ2 (including extrema at λ1 and λ2) is subtracted by 1. A retardation R by a birefringence is expressed by the following equation based on the equation (3):

$$R = (M-1)/2/(1/\lambda 1 - 1/\lambda 2) \tag{4}$$

Therefore, if two wavelengths λ1, λ2 at which a spectrum of transmitted light shows extrema and the number M of extrema which are present between the two wavelengths λ1, λ2 are obtained, a retardation R caused by a birefringence can be computed according to the equation (4) from the three parameters. Besides, a birefringence Δn=R/d can be computed.

When the extrema are either maxima or minima, a retardation R by a birefringence can be computed according to the following equation (5):

$$R = (N-1)/(1/\lambda 1 - 1/\lambda 2) \tag{5}$$

wherein N is the number of one of maxima and minima between the first and second extrema λ1, λ2. A birefringence Δn=R/d can be computed based on the retardation R.

In a birefringence measuring method according to the present invention, a spectrum of transmitted light from a light detecting element is measured by a multi-channel spectrometer which enable a high speed production of a spectrum and three parameters of a first extremum wavelength λ1 and a second extremum wavelength λ2 assuming extrema in the transmitted light spectrum, and the number M or N (including extrema of the first and second extremum wavelengths λ1, λ2) of extrema between the first and second extremum wavelengths λ1, λ2 are computed by a retardation computing circuit for outputting results of detection of the three parameters of a first extremum wavelength λ1 and a second extremum wavelength λ2 assuming extrema in the transmitted light spectrum, and the number M or N (including extrema of the first and second extremum wavelengths λ1, λ2) of extrema between the first and second extremum wavelengths λ1, λ2.

In the computer which compute a retardation R by a birefringence according to the equation (4) or (5) based on the three parameters, a retardation R by a birefringence of a film inserted between a polarizing element and a light detecting element can be computed from three parameters computed by a retardation computing circuit for outputting results of detection of the three parameters of a first extremum wavelength λ1 and a second extremum wavelength λ2 assuming extrema in the transmitted light spectrum, and the number M or N (including extrema of the first and second extremum wavelengths λ1, λ2) of extrema between the first and second maximum wavelengths, that is the first and second extremum wavelengths λ1, λ2 and the number M or N of extrema (including extrema at the first and second extremum wavelengths λ1, λ2) between the first and second extremum wavelengths λ1, λ2. At this time, parameters which are necessary for determining a birefringence of a film are in real time computed in the retardation computing circuit for outputting results of detection of the three parameters of a first extremum wavelength λ1 and a second extremum wavelength λ2 assuming extrema in the transmitted light spectrum, and the number M or N (including extrema of the first and second extremum wavelengths λ2, λ2) of extrema between the first and second extremum wavelengths and thereby a load in computation to be imposed in the computer for computing a birefringence can be reduced and as a result, a birefringence can be computed in real time.

Figure 2:
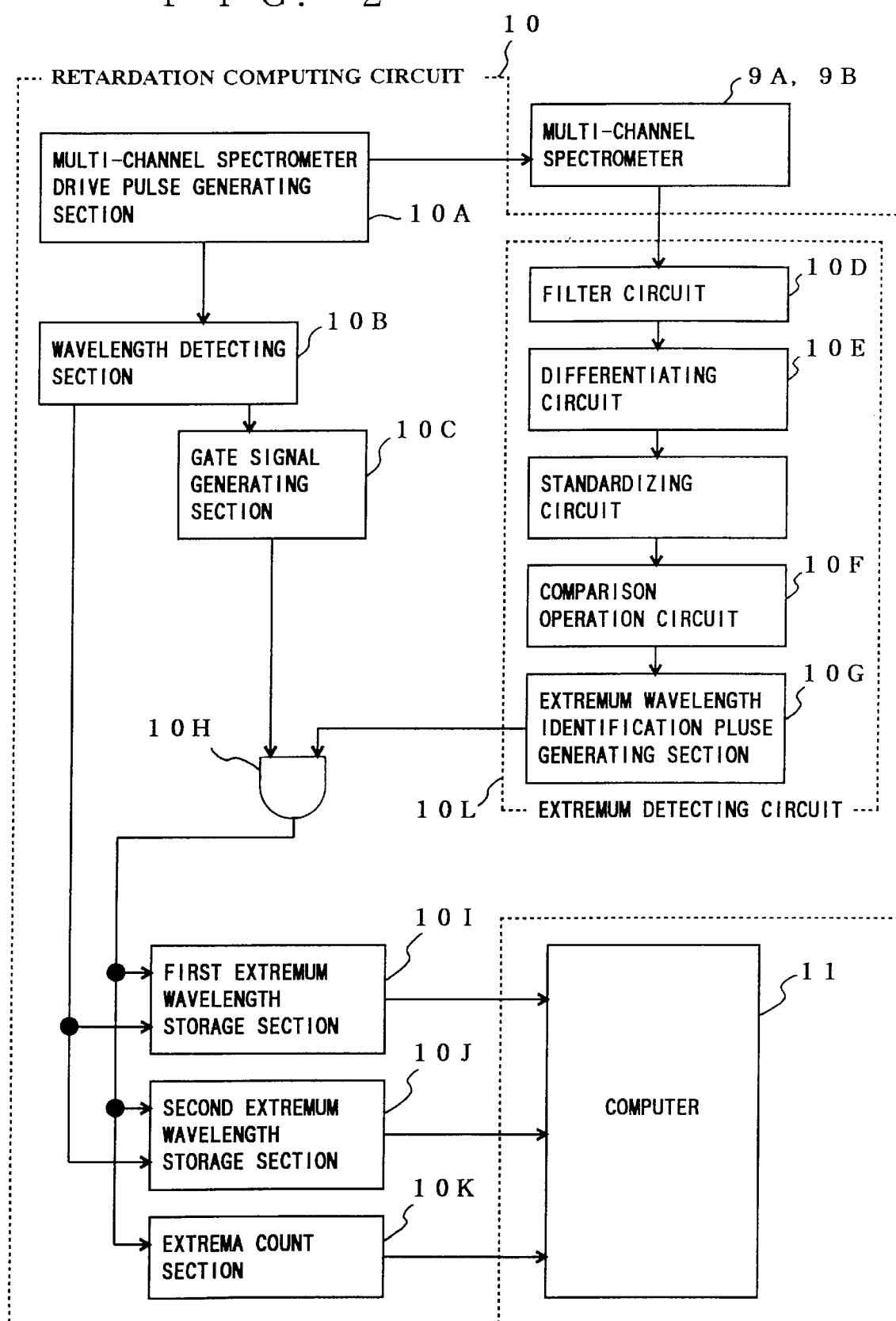
FIG. 2 is a view showing a degree of orientation computer.

In a birefringence measuring method according to the present invention, as shown in FIG. 2, there are generated a pulse for drive of CCD of a multi-channel spectrometer in a pulse generating section 10A and a pulse which synchronize with a data output time from each channel corresponding to a wavelength of CCD used in the retardation computing circuit (hereafter indicated by the same numeral mark 10 as the retardation computing processor) constituting a retardation computing processor 10. The multi-channel spectrometer 9A, 9B outputs a signal corresponding to a spectrum of transmitted light according to a CCD drive pulse output from a pulse generating section 10A. The signal output from the multi-channel spectrometer 9A, 9B is input to an extremum detecting circuit 10L of the retardation computing circuit 10 and the extremum detecting circuit 10L makes the signal input from the multi-channel spectrometer 9A, 9B pass through a filter circuit 10D, a differentiating circuit 10E, and comparator 10F and the extremum wavelength identification pulse generating section 10G and thereby a pulse at a time corresponding to a wavelength showing an extremum.

A pulse synchronizing with a data output time from each channel of CCD generated in the multi-channel spectrometer drive pulse generating section 10A is sent to the wavelength detecting section 10B and counting of the channel number of CCD corresponding to a wavelength is conducted. One of the count numbers of the channel numbers of CCD, which is an output from the wavelength detecting section 10B, is sent to the gate signal generating section 10C. In the gate signal generating section 10C, a wavelength range which detects a wavelength showing an extremum is set, and a gate signal is generated at a time corresponding to the wavelength range. A pulse generating at a time corresponding to a wavelength showing an extremum output after passing through the extremum detecting circuit 10L and a gate signal generating at a time corresponding to a wavelength range in which detection of a wavelength showing an extremum is conducted are input to an AND processing section 10H.

Since a logical operation is carried out between the two signals in the AND processing section 10H, a pulse output at a time corresponding to a wavelength showing an extremum is output only in a wavelength range, in which detection of a wavelength showing an extremum is conducted, from the AND processing section 10H. An output from the AND processing section 10H is input to the first extremum wavelength storage section 10I, the second extremum wavelength storage section 10J and the extrema count section 10K.

The count number of the CCD channel numbers which is an output from the wavelength detecting section 10B is input to the first extremum wave length storage section 10I and the second extremum wave length storage section 10J as well.

In the first extremum wavelength storage section 10I, a channel number corresponding to an extremum wavelength is stored when a first pulse of pulses generating at a time corresponding a wavelength showing an extremum output from the AND processing section 10H is input to the first extremum wavelength storage section 10I. Besides, the channel number stored is output in a synchronizing manner at the end of a gate signal.

In the second extremum wavelength storage section 10J, a channel number corresponding to an extremum wavelength is stored each time when a pulse generating at a time corresponding a wavelength showing an extremum output from the AND processing section 10H is stored to the second extremum wavelength storage section 10J. Besides, the channel number lastly stored is output in a synchronizing manner at the end of a gate signal.

In the extrema count section 10K, a pulse generating at a time corresponding to a wavelength showing an extremum output from the AND processing section 10H is counted and the count number is output in a synchronizing manner at the end of a gate signal.

After all, the outputs from the retardation computing circuit 10 are three parameter of a first extremum wavelength λ1 and a second extremum wavelength λ2 assuming extrema in a set range of wavelength of transmitted light, and the number M or N (including extreme of the first and second extremum wavelengths λ1, λ2) of extrema between the first and second extremum wavelengths.

After the three parameters are input to the computer 11 through a digital input interface or the like from the retardation computing circuit 10 and the channel number of CCD is converted to a wavelength, the computer 11 computes a retardation $R(=\Delta n \cdot d)$ according to the equations (4) or (5).

According to the birefringence measuring method of the embodiment, three parameters which are necessary for computation of a birefringence retardation, that is three parameters of a first extremum wavelength λ1 and a second extremum wavelength λ2 assuming extrema in the transmitted light spectrum, and the number M (including extrema of the first and second extremum wavelengths λ1, λ2) of extrema between the first and second extremum wavelengths can be detected and output in real time and moreover, if the three parameters are detected by an exclusive use of retardation computing circuit, a load in the computer is reduced, whereby a measurement of a birefringence in real time can be possible.

A birefringence $\Delta n$ is computed from a retardation R by a birefringence and a film thickness d obtained from the thickness gauges 8A, 8B.

Figure 3:
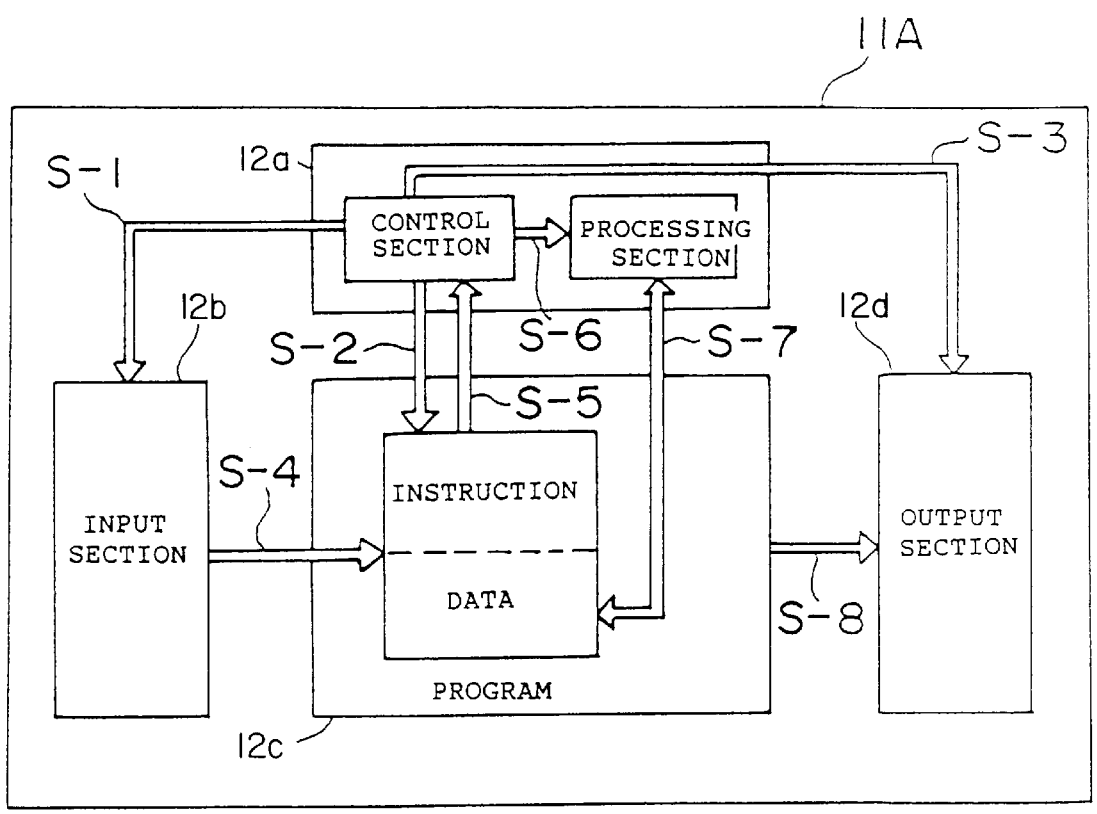
FIG. 3 is a block diagram showing a constitution of control apparatus.

As for a film orientation measuring apparatus for measuring an degree of orientation, an optical measuring apparatus can be used, which comprises: a spectrum producing/detecting apparatus, a fiber switch unit connected to the spectrum producing/detecting apparatus by fibers for light reception; a plurality of fibers for light reception each having a polarizing unit at the fore ends through a depolarization unit and connecting to a fiber switch unit; and a plurality of fibers for light projection having a polarizing unit at the fore ends through a depolarization cancel unit and connecting to a halogen lamp.

iii) The computer 11 which conducts computation according to the equation (3) uses a personal computer (hereinafter referred to as P11) and, as shown in FIG. 1, comprises: a PC body 11A; a key board 11B connected to the PC body 11A; and a display 11C. The PC body 11A, as shown in FIG. 3, comprises: a central processing unit 12a (hereinafter referred to as CPU); a main internal memory 12c (hereinafter referred to as memory); an input section 12b; and output section 12d.

The CPU 12a comprises: a processing section in which four operations, a logical processing, a logical comparison and the like are conducted; a control section in which an instruction is fetched from the memory 12c based on an address of the instruction and the content of the instruction is decoded and a necessary operational command is output to other apparatuses.

The control section sends an input control command to the input section 12b (S-1), sends a memory control command to the memory 12c (S-2) and sends an output control command to the output section 12d (S-3). A command input from the input section 12b is first transferred to the memory 12c (S-4), then data and an instruction is selected, and the selected data and the instruction are transferred to the control section of the CPU 12a in the memory 12c (S-5).

Thereafter, in the control section, the data and instruction transferred from the memory 12c are decoded and the control section gives a necessary operational command to the processing section (S-6). In the processing unit, four operations, a logical processing, a logical comparison and the like are conducted ON the given data and instruction.

In such a manner, the data and the instruction processed in the CPU 12a are again fed back to the memory 12c (S-7) and the result is transferred to the output section 12d (S-8).

The control section sequentially repeats a process comprising [fetching an instruction→decoding→address computation→fetching a data→execution an instruction] and thus a series of instructions are executed.

The PC 11 has correlation between the preset thickness or degree of orientation and the longitudinal draw ratio or lateral draw ratio in a format of a map stored in the memory 12c. The map makes it possible, for example to use an X abscissa to plot the thickness thereon and a Y ordinate to plot the rotational speed of a roll thereon, to use an X abscissa to plot the degree of orientation of a left side film thereon and a Y ordinate to plot a draw angle of a left side film with respect to a longitudinal center line thereon, to use an X abscissa to plot the degree of orientation of a right side film thereon and a Y ordinate to plot a draw angle of a right side film with respect to a longitudinal center line thereon.

At this point, when thicknesses and degree of orientations measured by the measuring apparatuses are input to the PC 11, comparison processing is conducted with preset values in advance.

When an error is produced between measured thickness or degree of orientation and corresponding values on the map, instruction is output to the drawing system so as to correct the error. When measured thickness and degree of orientation fall in the range of corresponding values on the map, a draw operation is repeated under a current condition unchanged.

In such a manner, PC 11 continuously conducts operations from measurement to comparative processing and to outputting a predetermined instruction in a time series manner with a predetermined interval.

iv) A control operation to change a longitudinal draw ration for a longitudinal drawing machine 5 will be described when an error is produced on a film thickness and a degree of orientation after longitudinal drawing.

A thickness and degree of orientation are measured in such a manner that a film is divided in measurement to predetermined blocks and measurements are conducted in each block in real time.

In the case where a thickness measured in a block by a thickness gauge 8A disposed at a downstream position of the longitudinal drawing machine 5 is larger than a preset value, the following means are taken.

Figure 4:
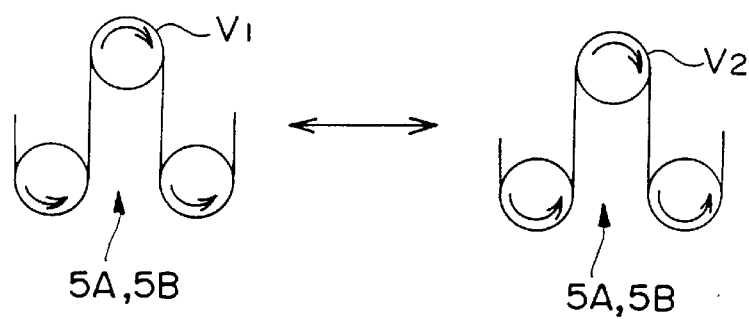
FIG. 4 is a representation illustrating a speed control of low and high speed rolls.

As first means, as shown in FIG. 4, a difference in rotational speed between a low speed roll 5A and a high speed roll 5B is increased. That is, the low speed roll 5A is set at a lower speed V1 and a high speed roll 5B is set at a higher speed V2 to increase a tension.

Figure 5:
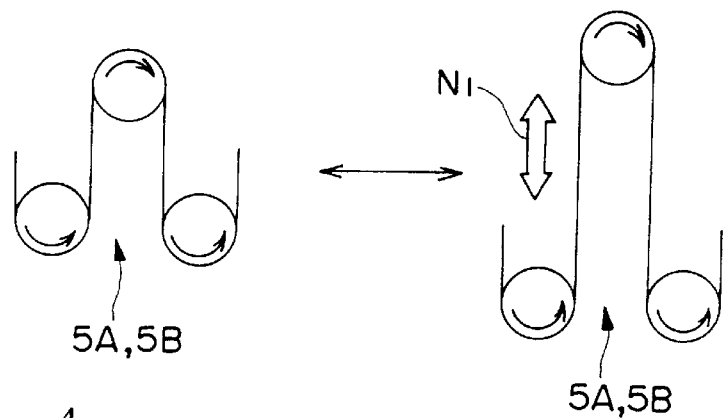
FIG. 5 is a representation illustrating a distance adjustment in directions, upward or downward, of low and high speed rolls.
Figure 6:
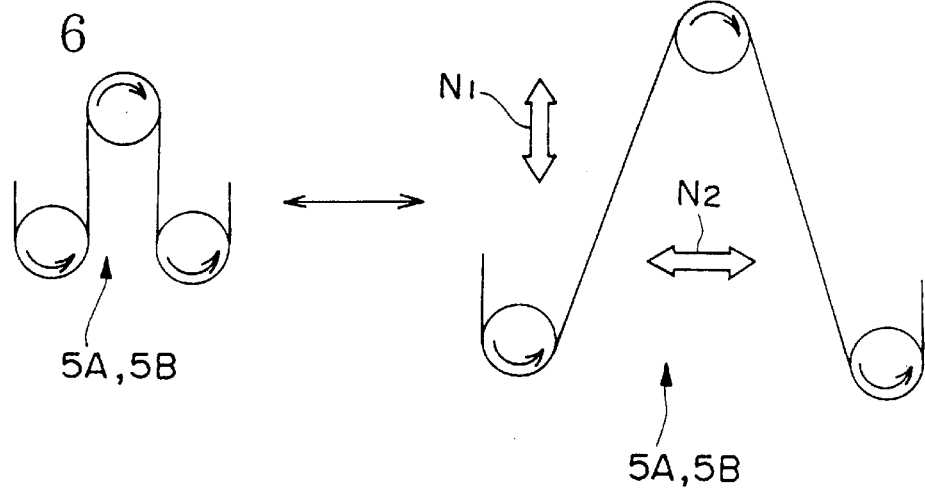
FIG. 6 is a representation illustrating distance adjustment in directions, upward or downward, and leftward or rightward, of low and high speed rolls.

Then, as second means, as shown in FIGS. 5 and 6, one or both of one pair of a low speed roll 5A and a high speed roll 5B among two or more pairs are displaced along a direction or directions, upward or downward, or leftward or rightward, so as to move both of the one pair away from each other in order that a draw gap and draw angle between the low speed roll 5A and high speed roll 5B are increased and thereby a tension to act on the film is increased.

That is, forces N1, N2 acting to move away the rolls 5A, 5B from each other are added to the system to grow an intensity of drawing and to increase a tension acting on the rolls 5A, 5B.

In this case, a draw gap for each roll is preferably changed in the range several mm to several cm. The reason why is that as a draw speed is higher, a length of the draw gap has to be smaller and further if a draw gap is large by too much a change, a probability of break-down of a film is larger.

Figure 7:
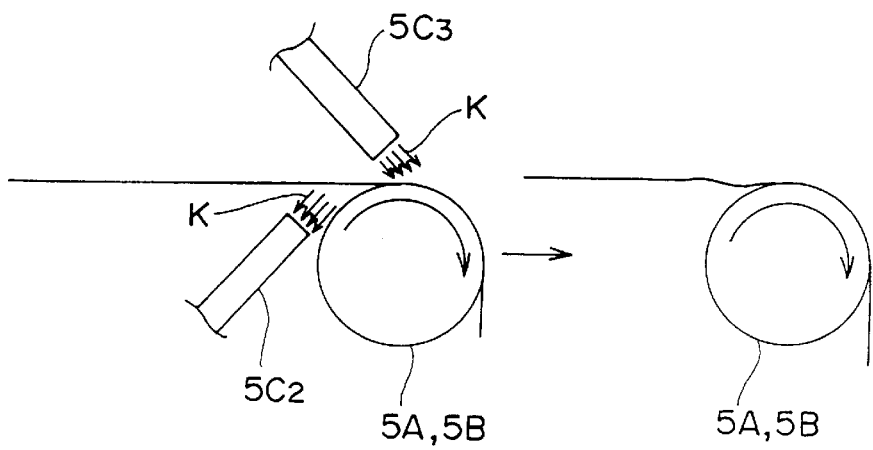
FIG. 7 is a representation illustrating air jets to low and high speed rolls.

As third means, in order to increase a press bonding strength to the low or high speed roll 5A, 5B, air K is removed from a close contact interface of a film with one or both rolls of the low and high rolls by sucking gas, such as air, through an air conditioner $5C_2$ as shown FIG. 7 and simultaneously air K rotated up by the rolls 5A, 5B is sucked, and air is jet from an air conditioner $5C_3$ to the film so as to press the film to a roll.

A press bonding force can be increased by heating the rolls 5A, 5B and a film with hot air jet or a flame shot from an air conditioner $5C_3$ as well.

As fourth means, a rotational speed of a screw inserted inside the extruder 2 is adjusted to a lower level by the screw rotational speed adjusting apparatus 13.

As fifth means, an opening degree of the die 3 mounted to the extruder 2 is narrowed by the die adjusting means 12. If the first and second means can be used, a feed of a molding material is reduced.

The first to fifth means can singularly or in combination be used.

Next, in the case where a film thickness in each block measured by the thickness gauge 8A disposed at a downstream position of the longitudinal drawing machine 5 is smaller than a preset value, the following means are taken.

At first, a difference in rotational speed between the low speed roll 5A and high speed roll 5B is made smaller. That is, the low speed roll 5A is accelerated to a higher speed V2 and the high speed roll 5B is slowed to a lower speed V1 to weaken a tension (first means).

In order to reduce a tension in a film, one or both of one pair of a low speed roll 5A and a high speed roll 5B among two or more pairs are displaced along a direction or directions, upward or downward, or leftward or rightward, so as to move both of the one pair closer to each other (a second means).

Figure 8:
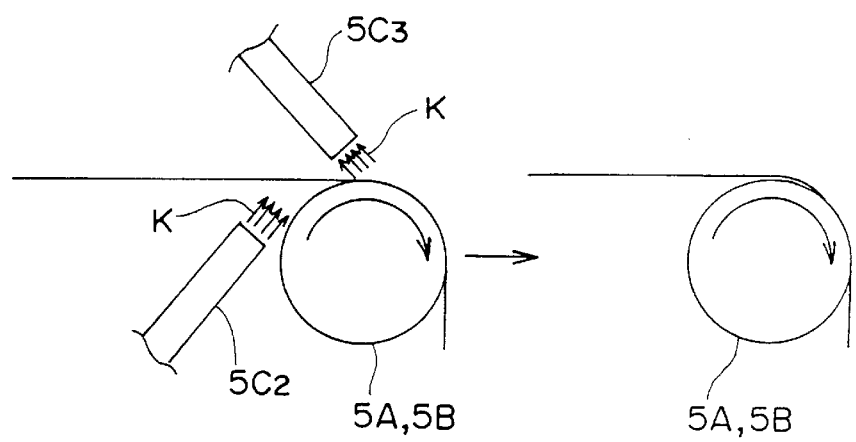
FIG. 8 is a representation illustrating air suctions at low and high speed rolls.

Air K is jet into a close contact interface of a film with one or both rolls of the low and high rolls 5A, 5B from the air conditioner $5C_2$ as shown in FIG. 8 and an air layer in a tiny clearance between the film 14 and the rolls 5A, 5B is formed by sucking air K from the air conditioner $5C_3$ is formed to decrease a press bonding force. A cold wind is jet from the air conditioner $5C_2$ to remove heat from the rolls 5A, 5B and the film 14 and thereby the bonding force can be reduced (third means).

A rotational speed of a screw inserted inside the extruder 2 is increased by the screw rotational speed adjusting apparatus 13 (fourth means).

An opening degree of the die 3 mounted to the extruder 2 is broadened by the die adjusting apparatus 12 (fifth means).

Then, in the case where a degree of orientation in a block measured by the orientation measuring apparatus disposed at a downstream of the longitudinal drawing machine 5 is smaller than a preset value, the following means are taken.

At first, increase the difference in rotational speed between the low and high rolls 5A, 5B (first means). That is, the low speed roll 5A is slowed to a lower speed V1 and the high speed roll 5B is accelerated to a higher speed V2 to strengthen a tension.

Then in order to increase a tension to the film, one or both of one pair of a low speed roll 5A and a high speed roll 5B among two or more pairs are displaced along a direction or directions, upward or downward, or leftward or rightward, so as to move both of the one pair away from each other (second means).

Air K is sucked through the air conditioner $5C_2$ and air K is removed from the close contact interface between one or both of the low and high speed rolls 5A, 5B with the film and simultaneously air rotated up by the rolls 5A, 5B as shown in FIG. 7. A hot wind is jet or a flame is shot by the air conditioner $5C_3$ to the rolls 5A, 5B and the film to strengthen a press bonding force by heating (third means).

Besides, a rotational speed of a screw inserted inside the extruder 2 is lowered by the screw rotational speed adjusting apparatus 13 (fourth means). An opening degree of the die 3 mounted to the extruder 2 is narrowed by the die adjusting apparatus 12 (fifth means).

Then in the case where a degree of orientation of a film in a block measured by the film orientation measuring apparatus disposed at a downstream of the longitudinal drawing machine 5 is larger than a preset value, the following means are taken.

A difference in rotational speed between the low and high speed rolls 5A, 5B is adjusted to be smaller. That is, the low speed roll 5A is accelerated to a higher speed V2 and the high speed roll 5B is slowed down to a lower speed V1 to reduce a tension (first means).

In order to reduce a tension to a film, one or both of one pair of a low speed roll 5A and a high speed roll 5B among two or more pairs are displaced along a direction or directions, upward or downward, or leftward or rightward, so as to move both of the one pair closer to each other (second means).

Air K is jet into a close contact interface between one or both of the low and high speed rolls 5A, 5B and a film from the air conditioner $5C_2$ as shown in FIG. 8 and air K is sucked through the air conditioner $5C_3$ to form an air layer in a tiny clearance between the film 14 and the rolls 5A, 5B to weaken a press bonding force. It is possible that a cold air is jet from $5C_3$ to remove heat from the rolls 5A, 5B and the film to weaken a press bonding force (third means).

A rotational speed of a screw inserted inside the extruder 2 is increased by the screw rotational speed adjusting apparatus 13 (fourth means). An opening degree of the die 3 mounted to the extruder 2 is broadened by the die adjusting apparatus 12 (a fifth means).

These control means are to change a longitudinal draw ratio in the case where errors are produced in a thickness measured in the thickness measuring apparatus 8A disposed at a downstream position of the longitudinal drawing machine 5 and in an degree of orientation measured by the film orientation measuring apparatus disposed at the downstream position, but in the case where errors are produced in a thickness measured by the thickness measuring apparatus 8B disposed at a downstream position of the lateral drawing machine 6 and in an degree of orientation measured by the film orientation measuring apparatus, these control means can be used as well.

The Second Embodiment (3) Next, an oriented film producing facility according to the second embodiment will be described.

Since a constitution of an oriented film producing facility 1 according to the second embodiment and control operations of an control apparatus 11 thereof are the same as those of the first embodiment and the description is omitted. With respect to measurement of a thickness and degree of orientation, a film is divided to a predetermined blocks and the thickness and degree of orientation are measured on each block in real time.

Then, in the case where an error arises in thickness after lateral drawing, a control operation to change a lateral draw ratio for the lateral drawing machine 6 will be described.

First, in the case where a thickness of a film in a block measured by the thickness gauge 8B disposed at a downstream position of the lateral drawing machine 6 is larger than a preset value, the following means are taken.

Figure 9:
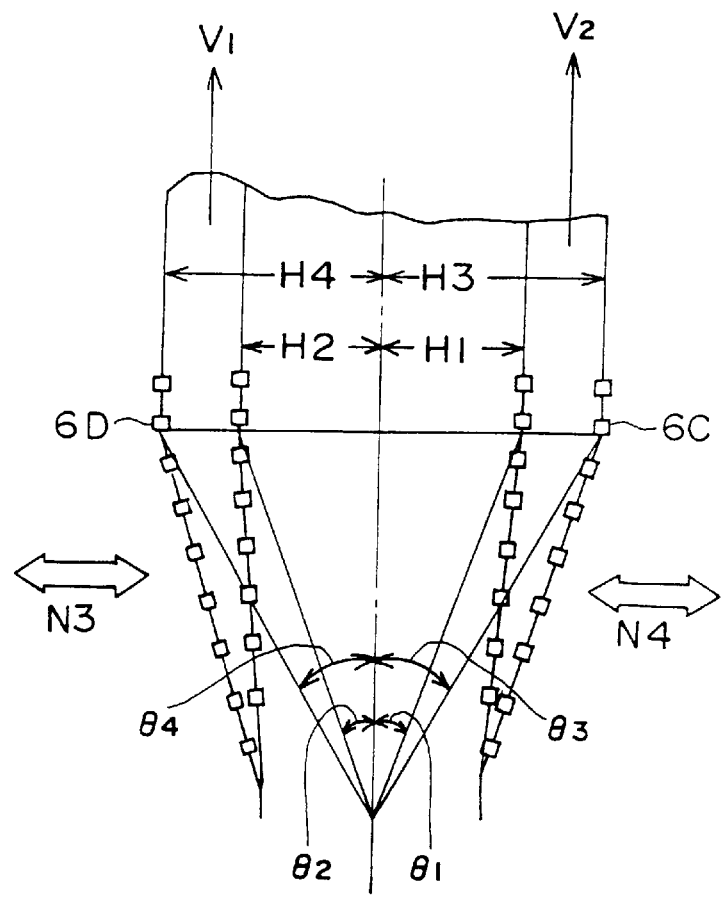
FIG. 9 is a representation illustrating adjustment in drawing in a lateral drawing machine.

As first means, in order to increase a lateral draw angle in lateral drawing as shown in FIG. 9, if a film thickness of a right side with respect to a center line of the film is larger, a draw angle θ1 in the right direction is increased to θ3 and a draw width H1 is extended to a given draw width H3.

If a film thickness of a left side with respect to the center line is larger, a draw angle θ2 in the left side is increased to θ4 and a draw width H2 is extended to a given draw width H4.

Furthermore, if thicknesses of both directions in right and left sides are larger, draw angles θ1, θ2 in right and left sides are respectively increased to θ3, θ4 and draw widths H1, H2 are respectively extended to H3, H4.

As second means, a lateral draw force in the left or right side film is strengthen by changing a speed of running rails 6E, 6F mounted with clips 6C, 6D in a fine manner. As third means, a heater for heating a film is divided into squares like those of a checker board as shown in FIG. 10 and a temperature of a block corresponding to a film block having a larger thickness is raised.

As fourth means, a rotational speed of a screw inserted inside the extruder 2 is adjusted to a lower speed by the screw rotational speed adjusting apparatus 13.

As fifth means, an opening degree of the die 3 mounted to the extruder 2 is narrowed by the die adjusting apparatus. The first to fourth means are used singly or in combination.

Then, in the case where a thickness in a block of a film measured by the thickness gauge 8B disposed at a downstream position of the lateral drawing machine 6 is smaller than a preset value, the following means are taken.

First, in order to reduce a lateral draw angle in lateral drawing, as shown in FIG. 9, if a film thickness in the right side with respect to a center line is smaller, a draw angle in the right side θ3 is decreased to θ1 and a draw width H3 is narrowed to a given draw width H1.

If a film thickness in a left side n with respect to the center line of the film is smaller, a draw angle in the left side θ4 is reduced to θ2 and a draw width H4 is narrowed to a given draw width H2.

If both of film thicknesses in a right and left sides of the film are smaller, both draw angles θ3, θ4 are respectively decreased to θ1, θ2 and draw widths H3, H4 are respectively narrowed to H1, H2 (first means).

A lateral draw force in the left or right side film is weakened by changing a speed of running rails 6E, 6F mounted with clips 6C, 6D in a fine manner (second means). A heater for heating a film is divided into squares like those of a checker board as shown in FIG. 10 and a temperature of a block corresponding to a film block having a smaller thickness is lowered (third means).

Moreover, for example it is possible that if a thickness is small, a draw angle is reduced and a draw width is narrowed, and if a thickness is large, a draw angle is increased and a draw width is extended. If a degree of orientation is large, a draw angle is decreased and a draw width is narrowed, and if an degree of orientation is small, a draw angle is increased and a draw width is extended.

A rotational speed of a screw inserted inside the extruder 2 is adjusted to a higher speed by the screw rotational speed adjusting apparatus 13 (fourth means). An opening degree of the die 3 mounted to the extruder 2 is broadened by the die adjusting apparatus (fifth means).

Then, in the case where a degree of orientation in a block of a film measured by the film orientation measuring apparatus disposed at a downstream position of the lateral drawing machine 6 is smaller than a preset value, the following means are taken.

First, in order to increase a lateral draw angle in lateral drawing, as shown in FIG. 9, if an degree of orientation in the right side with respect to a center line is smaller, a draw angle in the right side θ1 is increased to θ3 and a draw width H1 is extended to a given draw width H3.

If an degree of orientation in a left direction with respect to the center line of the film is smaller, a draw angle in the left direction θ2 is increased to θ4 and a draw width H2 is extended to a given draw width H4.

If both of film thicknesses in a right and left sides of the film are smaller, both draw angles θ1, θ2 are respectively increased to θ3, θ4 and draw widths H1, H2 are respectively extended to H3, H4 (first means).

A lateral draw force in the left or right side film is strengthened by changing a speed of running rails 6E, 6F mounted with clips 6C, 6D in a fine manner (second means). A heater for heating a film is divided into squares like those of a checker board as shown in FIG. 10 and a temperature of a block corresponding to a film block having a smaller degree of orientation is lowered (third means).

A rotational speed of a screw inserted inside the extruder 2 is adjusted to a lower speed by the screw rotational speed adjusting apparatus 13 (fourth means). An opening degree of the die 3 mounted to the extruder 2 is narrowed by the die adjusting apparatus (fifth means).

Then, in the case where a degree of orientation in a block of a film measured by the film orientation measuring apparatus disposed at a downstream position of the lateral drawing machine 6 is larger than a preset value, the following means are taken.

First, in order to decrease a lateral draw angle in lateral drawing, as shown in FIG. 9, if an degree of orientation in the right side with respect to a center line is larger, a draw angle in the right side θ3 is decreased to θ1 and a draw width H3 is narrowed to a given draw width H1.

If an degree of orientation in a left side with respect to the center line of the film is larger, a draw angle in the left side θ4 is decreased to θ2 and a draw width H4 is narrowed to a given draw width H2.

If both of degree of orientations in a right and left sides of the film are larger, both draw angles θ3, θ4 are respectively decreased to θ1, θ2 and draw widths H3, H4 are respectively narrowed to a given draw with H1, H2 (first means).

A lateral draw force in the left or right side film is weakened by changing a speed of running rails 6E, 6F mounted with clips 6C, 6D in a fine manner (second means). A heater for heating a film is divided into squares like those of a checker board as shown in FIG. 10 and a temperature of a heater block corresponding to a film block having an smaller thickness is lowered (third means).

A rotational speed of a screw inserted inside the extruder 2 is adjusted to a higher speed by the screw rotational speed adjusting apparatus 13 (fourth means). An opening degree of the die 3 mounted to the extruder 2 is broadened by the die adjusting apparatus 12 (fifth means).

These control means are to change a lateral draw ratio in the case where errors are produced in a thickness measured in the thickness measuring apparatus 8B disposed at a downstream position of the lateral drawing machine 6 and in an degree of orientation measured by the film orientation measuring apparatus disposed at the downstream position, but in the case where errors are produced in a thickness measured by the thickness gauge 8A disposed at a downstream position of the longitudinal drawing machine 5 and in an degree of orientation measured by the film orientation measuring apparatus, these control means can be used as well.

A lateral draw ration can be changed by use of a control means according to the first embodiment.

Figure 11:
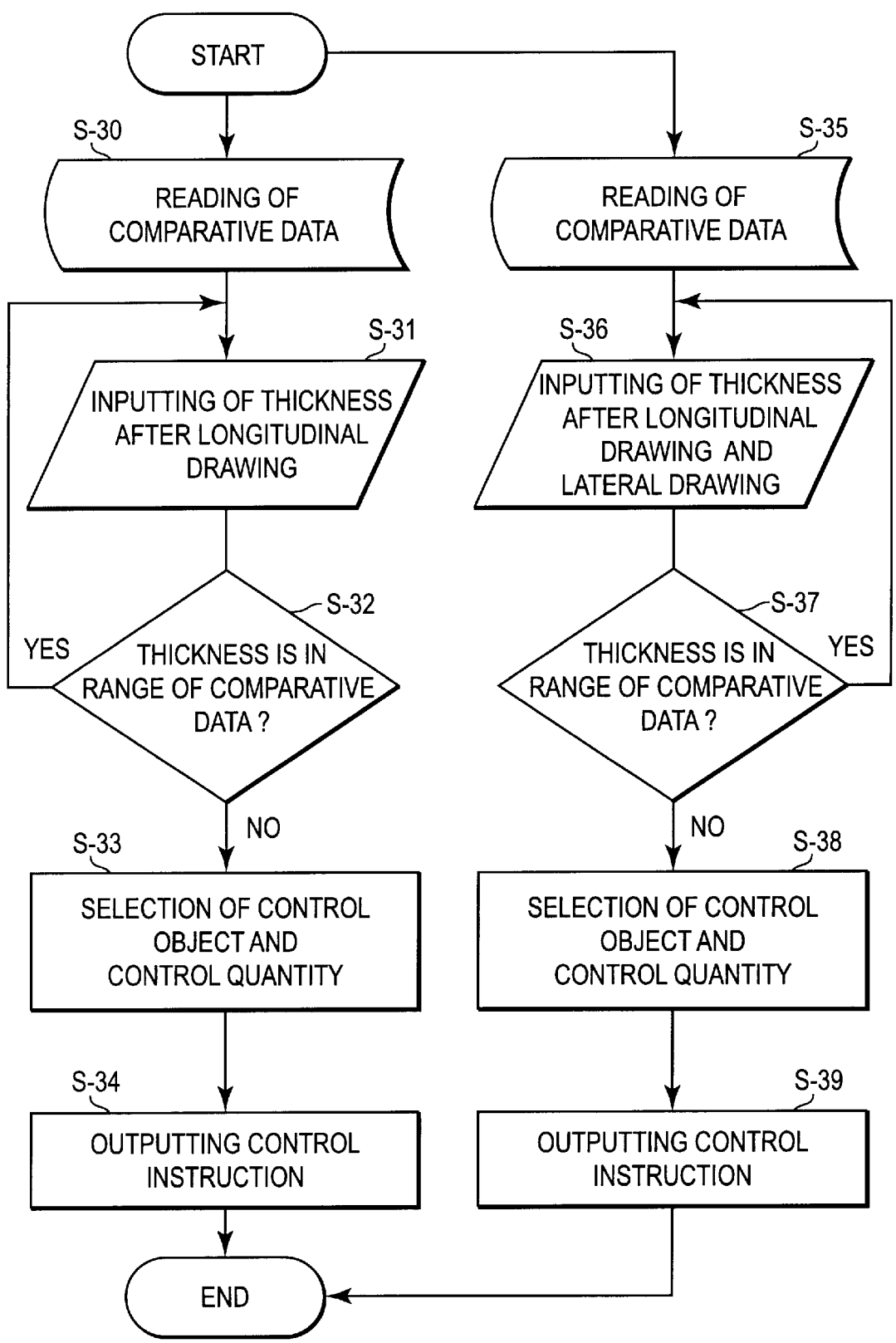
FIG. 11 is a flow chart showing a control operation for a longitudinal drawing machine.
Figure 12:
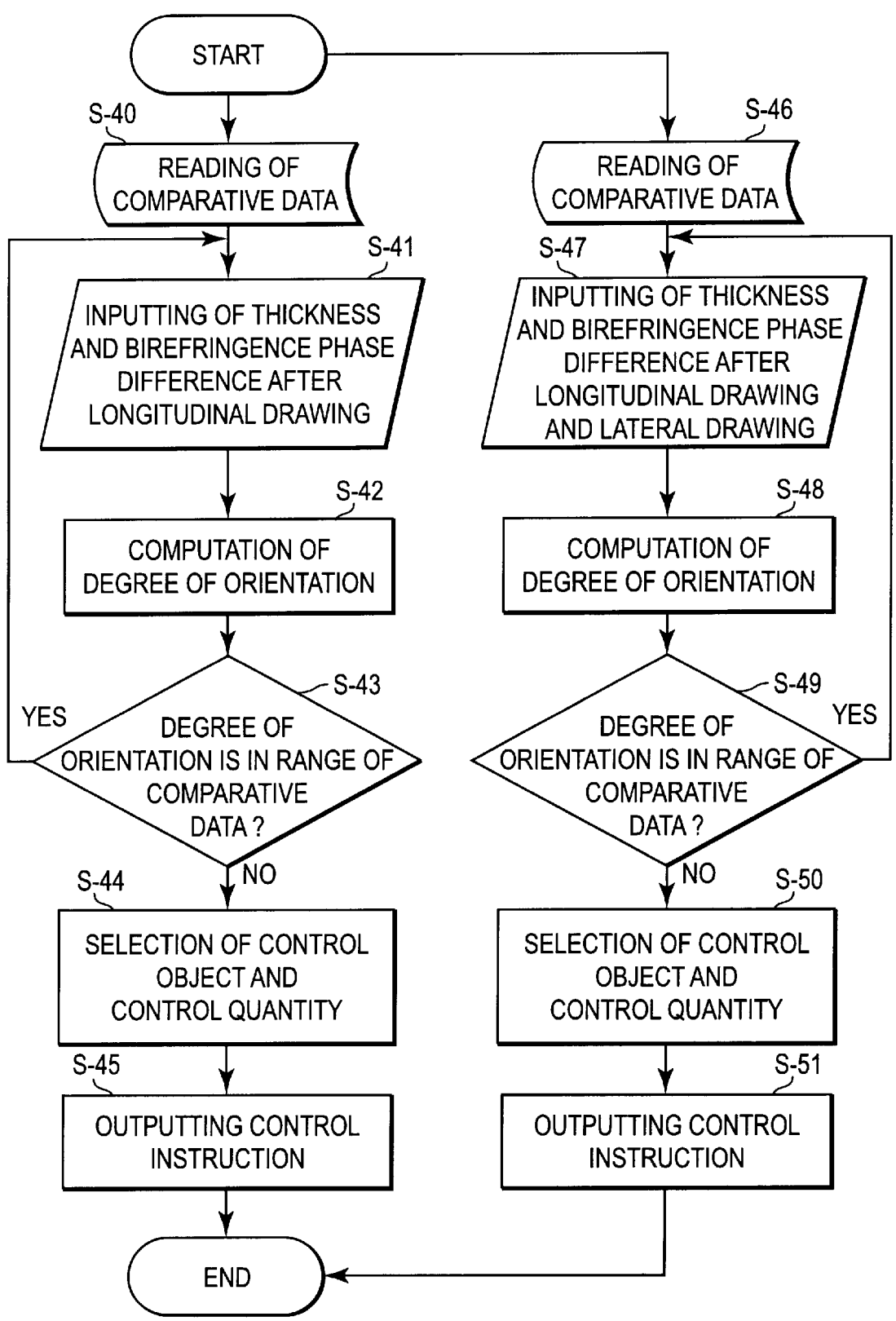
FIG. 12 is a flow chart showing a control operation for a lateral drawing machine.
Figure 13:
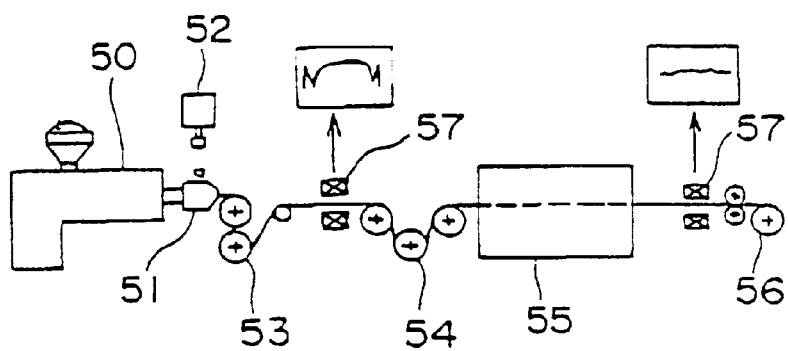
FIG. 13 is a view showing a drawing machine in accordance with the background art.

(4) A control operation by the control apparatus 11 will be described in reference to flow charts shown in FIGS. 11, 12.

First of all, the case where a predetermined control is conducted in a drawing system through comparison of a thickness will be described in reference to FIG. 11. When a control operation is started, a program stored in a memory of the PC 11 is activated and a target value after longitudinal drawing is read to a register as a comparative data (step 30). The thickness gauge 8A disposed at a downstream position of the longitudinal drawing machine 5 measures a film thickness after longitudinal drawing on each block of the film and outputs the measured value. The measured thickness is input to the PC 11 (step 31) and comparison processing is conducted between the comparative data and a thickness (step 32).

As a result, if the thickness falls in the range of a comparative data, a current state is maintained and a thickness measured is read from the thickness gauge 8A (step 31) to conduct comparative processing (step 32). Here, the thickness gauge 8 measures a thickness at a predetermined interval based on a timing pulse generated by a CCD timing pulse generating section to input the measured thickness to the PC 11 as occasion demands.

A comparison processing is conducted and as a result, if a thickness is larger or smaller than a comparative data, a control object and a control quantity to be output to the drawing system are selected (step 33). A predetermined control command is output to the drawing system based on the selection result (step 34).

Target values after longitudinal and lateral drawings are read to a register as comparative data (step 35). The thickness gauge 8B disposed at a downstream position of the lateral drawing machine 6 measures thickness of a film after the longitudinal and lateral drawings on each block and outputs the measured values. The thickness measured is input to the PC 11 (step 36) and comparison processing is conducted between the comparative data and the thickness (step 37).

As a result, if the thickness falls in the range of a comparative data, a current state is maintained and a thickness measured is read from the thickness gauge 8B (step 36) to proceed to comparison processing (step 37).

A comparison processing is conducted and as a result, if a thickness is larger or smaller than a comparative data, a control object and a control quantity to be output to the drawing system are selected (step 38). A predetermined control command is output to the drawing system based on the selection result (step 39).

The case where a predetermined control is conducted in a drawing system through comparison of an degree of orientation will be described in reference to FIG. 12. When a control operation is started, a target value after longitudinal drawing stored in a memory of the PC 11 is read in a register as a comparative data (step 40).

A birefringence is computed in the retardation computing apparatus 10 for computing a retardation from a film thickness of each block from the thickness gauge 8A disposed at a downstream position of the longitudinal drawing machine 5 and optical information of transmitted light through each block of the film read from the spectrometer 9A and the birefringence retardation is input (step 41). An degree of orientation of each film block is computed from these parameters (step 42). Thereafter, comparative processing between the comparative data and the degree of orientation is conducted (step 43).

As a result, if the degree of orientation falls in the range of a comparative data, a current state is maintained and an degree of orientation is again computed from new parameters (step 42) and comparison processing is conducted (step 43). Here, measurement of parameters is conducted at a predetermined interval based on a timing pulse generated by the timing pulse generating section 10A and an degree of orientation is computed based on the parameters as occasion demands.

As a result of the comparison processing, if the degree of orientation is larger or smaller that the comparative data, a control object and a control quantity to be output to the drawing system are selected (step 44). A predetermined control demand is output to the drawing system based on the selection result (step 45).

Then target values after longitudinal and lateral drawings are read in a register as a comparative data (step 46). A birefringence retardation is computed in the retardation computing apparatus 10 for computing a retardation from a film thickness of each block from the thickness gauge 8A disposed at a downstream position of the lateral drawing machine 6 and optical information of transmitted light through each block of the film read from the spectrometer 9A and the birefringence retardation is input (step 47).

Then, an degree of orientation of each block film is computed from these parameters (step 48). Thereafter, comparison processing is conducted between the comparative data and the degree of orientation (step 49).

As a result of the comparison processing, if the degree of orientation falls in the range of a comparative data, a current state is maintained and an degree of orientation is again computed from new parameters (step 48) and comparison processing is conducted (step 49).

As a result of the comparison processing, if an degree of orientation is larger or smaller than a comparative data, a control object and a control quantity to be output to the drawing system are selected (step 50). A predetermined control command is output to the drawing system based on the selection result (step 51).

According to an oriented film producing facility of the present invention, a thickness and degree of orientation of a film after longitudinal drawing are independently measured on each blocks divided of the film in a continuous manner and a thickness and degree of orientation of a film after longitudinal and lateral drawings are independently measured on each blocks divided of the film in a continuous manner, and a predetermined control operation is conducted in the drawing system, whereby a thickness and degree of orientation of an oriented film are controlled in a uniform manner. Breakdown or the like of a film is, as describe above, prevented from occurring by controlling a thickness and degree of orientation in a uniform manner in a high speed molding.

Since a probability to be broken down or the like during drawing can be reduced, time and labor required can be saved in restoration from stoppage to restart for the drawing system when a film is broken down.

According to a birefringence measuring method of the present invention, three parameters required for computation of a birefringence retardation, that is three parameter of a first extremum wavelength $\lambda 1$ and a second extremum wavelength $\lambda 2$ assuming extrema in the transmitted light spectrum, and the number M (including extrema of the first and second extremum wavelengths $\lambda 1$, $\lambda 2$) of extrema between the first and second extremum wavelengths can be detected and output in real time and the three parameters are detected by an exclusive use of retardation computing circuit and thereby a load on a computer can be reduced and as a result, measurement of a birefringence in real time can be realized.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An oriented film producing facility comprising:
    a facility for melting a molding material;
    an extruder having a die for shaping the molding material to a not-oriented film;
    a base film molding apparatus for producing a base film by cooling the not-oriented film shaped through the die;
    a longitudinal drawing machine for drawing the cooled base film in a longitudinal direction with a low speed roll and a high speed roll;
    a lateral drawing machine for drawing the longitudinally drawn film in a lateral direction by holding both edges of the longitudinally drawn film;
    a thickness measuring apparatus for measuring a thickness of the longitudinally drawn film in real time after the cooled base film is drawn in the longitudinal direction and for generating a signal corresponding to the thickness measured;

a retardation measuring apparatus for measuring a retardation of the longitudinally drawn film caused by birefringence in real time after the cooled base film is drawn in the longitudinal direction, a computing apparatus for computing a degree of orientation of the longitudinally drawn film from the measured retardation by dividing the measured retardation by the measured thickness and for generating a signal corresponding to the computed degree of orientation; and a computer for processing the signals corresponding to the measured thickness and to the computed degree of orientation and for outputting a control signal to a control means for changing a longitudinal draw ratio in longitudinal drawing by the longitudinal drawing machine based on results of thickness and orientation comparison operations so that the measured thickness and the computed degree of orientation coincide with preset target values of thickness and degree of orientation to thereby control a drawing condition of the longitudinal drawing machine in accordance with the control signal wherein the computer comprises a thickness comparison means for performing the thickness comparison operation to compare a preset thickness with the measured thickness and an orientation comparison means for performing the orientation comparison operation to compare a preset degree of orientation with the computed degree of orientation.

2. An oriented film producing facility according to claim 1, wherein the control means adjusts an opening degree of the die lips in accordance with the control signal.

3. An oriented film producing facility according to claim 1, wherein the extruder includes a screw and the control means adjusts a screw speed of the extruder in accordance with the control signal.

4. An oriented film producing facility according to claim 1, further including a heating apparatus for heating the longitudinally drawn film in the lateral drawing which is divided into predetermined blocks wherein:

the thickness measured by the thickness measuring apparatus in real time corresponds to thicknesses of the film at each of the blocks, the retardation measured by the retardation measuring apparatus in real time corresponds to retardations of the film at each of the blocks, the computed degree of orientation computed by the computing apparatus corresponds to degrees of orientations at each of the blocks, the thickness comparison operation performed by the computer compares a preset thickness of each block with the measured thickness of each block, the orientation comparison operation performed by the computer compares a preset degree of orientation of each block with the computed degree of orientation of each block, and the computer outputs a control signal for each block to a control means for each block for changing the longitudinal draw ratio in longitudinal drawing by the longitudinal drawing machine based on results of thickness and orientation comparison operations for each block so that the measured thickness of each block and the computed degree of orientation of each block coincide with preset target values of thickness of each block and degree of orientation of each block to thereby control a drawing condition of the longitudinal drawing machine in accordance with the control signal for each block.

5. An oriented film producing facility according to claim 4, wherein the control means for each block controls a heating temperature of each block in accordance with the control signal output for each block.

6. An oriented film producing facility according to claim 1, wherein the control means for changing the longitudinal draw ratio adjusts a draw speed of the low and high speed rolls in the longitudinal drawing.

7. An oriented film producing facility according to claim 1, wherein the control means for changing the longitudinal draw ratio adjusts a draw gap between the low and high speed rolls in the longitudinal drawing.

8. An oriented film producing facility according to claim 1, wherein the control means for changing the longitudinal draw ratio adjusts draw angles of the low and high speed rolls in the longitudinal drawing.

9. An oriented film producing facility according to claim 1, wherein the control means for changing the longitudinal draw ratio adjusts a pressure force of the cooled base film acting upon the high speed roll and the low speed roll in the longitudinal drawing.

10. An oriented film producing facility according to any of claims 6 to 9, wherein:

the thickness measuring apparatus for measuring a thickness of the longitudinally drawn film measures the thickness of the longitudinally drawn film in respective divided regions of the longitudinally drawn film along a lateral direction thereof after the longitudinal drawing, the retardation measuring apparatus for measuring a retardation of the longitudinally drawn film measures the retardation of the longitudinally drawn film in respective divided regions of the longitudinally drawn film along the lateral direction thereof after the longitudinal drawing, and the computing apparatus for computing a degree of orientation of the longitudinally drawn film from the measured retardation computes a degree of orientation of the longitudinally drawn film for the respective divided regions of the longitudinally drawn film along the lateral direction thereof after the longitudinal drawing.

11. An oriented film producing facility comprising:

a facility for melting a molding material;

an extruder having a die for shaping the molding material to a not-oriented film;

a base film molding apparatus for producing a base film by cooling the not-oriented film shaped through the die;

a longitudinal drawing machine for drawing the cooled base film in a longitudinal direction with a low speed roll and a high speed roll;

a lateral drawing machine for drawing the longitudinally drawn film in a lateral direction by holding both edges of the longitudinally drawn film;

a thickness measuring apparatus for measuring a thickness of the laterally drawn film in real time after the longitudinally drawn film is drawn in the lateral direction and for generating a signal corresponding to the thickness measured;

a retardation measuring apparatus for measuring a retardation of the laterally drawn film caused by birefringence in real time after the longitudinally drawn film is drawn in the lateral direction, a computing apparatus for computing a degree of orientation of the laterally drawn film from the measured retardation by dividing the measured retardation by the measured thickness and for generating a signal corresponding to the computed degree of orientation; and a computer for processing the signals corresponding to the measured thickness and to the computed degree of orientation and for outputting a control signal to a control means for changing a lateral draw ratio in lateral drawing by the lateral drawing machine based on results of thickness and orientation comparison operations so that the measured thickness and the computed degree of orientation coincide with preset target values of thickness and degree of orientation to thereby control a drawing condition of the lateral drawing machine in accordance with the control signal wherein the computer comprises a thickness comparison means for performing the thickness comparison operation to compare a preset thickness with the measured thickness and an orientation comparison means for performing the orientation comparison operation to compare a preset degree of orientation with the computed degree of orientation.

12. An oriented film producing facility according to claim 11, wherein the control means for changing the lateral draw ratio adjusts a lateral draw angle in the lateral drawing.

13. An oriented film producing facility according to claim 11, wherein the control means for changing the lateral draw ratio adjusts a lateral draw speed in the lateral drawing.

14. An oriented film producing facility according to claim 11, wherein:

the thickness measuring apparatus for measuring a thickness of the laterally drawn film measures the thickness of the laterally drawn film in respective divided regions of the laterally drawn film along a lateral direction thereof after the lateral drawing, the retardation measuring apparatus for measuring a retardation of the laterally drawn film measures the retardation of the laterally drawn film in respective divided regions of the laterally drawn film along the lateral direction thereof after the lateral drawing, and the computing apparatus for computing a degree of orientation of the laterally drawn film from the measured retardation computes a degree of orientation of the laterally drawn film for the respective divided regions of the laterally drawn film along the lateral direction thereof after the lateral drawing.

15. An oriented film producing facility according to claim 14, wherein the control means adjust a heating temperature of the longitudinally drawn film in correspondence to blocks of a heating apparatus for heating the longitudinally drawn film in the lateral drawing, said blocks being formed by dividing the heating apparatus in a predetermined manner.

16. An oriented film producing facility according claims 1 or 11, wherein:

the thickness measuring apparatus measures the thickness of the film by use of near-infrared absorption, the thickness measuring apparatus outputs a signal corresponding to a thickness within 50 milliseconds, the retardation measuring apparatus measures a retardation based on a principle for measuring a transmitted light spectrum of a film sandwiched by polarizing elements, and the computing apparatus computes a birefringence and outputs a signal corresponding to the birefringence within 50 milliseconds.

* * * * *